(12) United States Patent
Cho et al.

(10) Patent No.: US 7,120,478 B2
(45) Date of Patent: Oct. 10, 2006

(54) BLOOD SUGAR LEVEL MEASURING APPARATUS

(75) Inventors: Ok-Kyung Cho, Schwerte (DE); Yoon-Ok Kim, Schwerte (DE)

(73) Assignee: Hitachi, Ltd., Tokyo (JP)

( * ) Notice: Subject to any disclaimer, the term of this patent is extended or adjusted under 35 U.S.C. 154(b) by 452 days.

(21) Appl. No.: 10/649,689

(22) Filed: Aug. 28, 2003

(65) Prior Publication Data

US 2005/0010094 A1   Jan. 13, 2005

(30) Foreign Application Priority Data

Jul. 11, 2003  (JP) .............................. 2003-195455

(51) Int. Cl.
*A61B 5/00* (2006.01)
(52) U.S. Cl. ..................................... 600/316
(58) Field of Classification Search ................ 600/310, 600/316, 322, 323, 326, 365, 549
See application file for complete search history.

(56) References Cited

U.S. PATENT DOCUMENTS

| | | | |
|---|---|---|---|
| 4,306,569 A | 12/1981 | Weil | |
| 4,333,803 A | 6/1982 | Seger | |
| 4,750,140 A | 6/1988 | Asano et al. | |
| 4,802,489 A | 2/1989 | Nitzan | |
| 5,551,422 A | 9/1996 | Simonsen | |
| 5,676,143 A | 10/1997 | Simonsen | |
| 5,725,480 A | 3/1998 | Oosta | |
| 5,732,711 A | 3/1998 | Fitzpatrick | |
| 5,743,262 A | 4/1998 | Lepper, Jr. | |
| 5,769,784 A | 6/1998 | Barnett | |
| 5,795,305 A | 8/1998 | Cho | |
| 5,924,996 A | 7/1999 | Cho | |
| 6,226,089 B1 | 5/2001 | Hakamata | |
| 6,240,306 B1 | 5/2001 | Rohrscheib | |
| 6,269,314 B1 | 7/2001 | Iitawaki et al. | |
| 6,280,381 B1 | 8/2001 | Malin | |
| 6,353,226 B1 | 3/2002 | Khalil | |
| 6,615,061 B1 | 9/2003 | Khalil | |
| 2002/0183646 A1 | 12/2002 | Stivoric et al. | |
| 2003/0152133 A1 | 8/2003 | Ellenz | |

FOREIGN PATENT DOCUMENTS

| | | |
|---|---|---|
| EP | 0 778 000 A1 | 6/1997 |
| JP | 06 317566 | 11/1994 |
| JP | 7-71945 | 3/1995 |
| JP | 08 322821 | 12/1996 |
| JP | 10-033512 A | 2/1998 |
| JP | 10-108857 | 4/1998 |
| JP | 11 505451 | 5/1999 |

(Continued)

OTHER PUBLICATIONS

"Facial And Sublingual Temperature Changes Following Intravenous Glucose Injection In Diabetics", Hillson, et al., Diabete & Metabolisme (Paris), 1982, 8, 15-19.

(Continued)

*Primary Examiner*—Eric F. Winakur
(74) *Attorney, Agent, or Firm*—Antonelli, Terry, Stout and Kraus, LLP.

(57) ABSTRACT

Blood sugar levels are non-invasively measured based on temperature measurements. An insulation structure is employed in a temperature measurement part for measuring heat amount and non-invasively obtained blood sugar level measurements are corrected by blood oxygen saturation and the volume of blood flow so that the measurement data can be stabilized and the measurement accuracy can be enhanced.

18 Claims, 20 Drawing Sheets

FOREIGN PATENT DOCUMENTS

| | | |
|---|---|---|
| JP | 11 155840 | 6/1999 |
| JP | 11-230901 | 8/1999 |
| JP | 11 318872 | 11/1999 |
| JP | 2000074829 | 3/2000 |
| JP | 2000506048 | 5/2000 |
| JP | 2000-258343 A | 9/2000 |
| JP | 2002535023 | 10/2002 |
| JP | 2003510556 | 3/2003 |
| WO | 01/28417 | 4/2001 |
| WO | WO 01/28414 | 4/2001 |
| WO | 03/010510 | 2/2003 |

OTHER PUBLICATIONS

"Diabetes Mellitus And Thermoregulation", Bennett, et al., Can. J. Physiol. Pharmacol., 65, pp. 1365-1376, 1987.

FIG.10(a)
FIG.10(b)
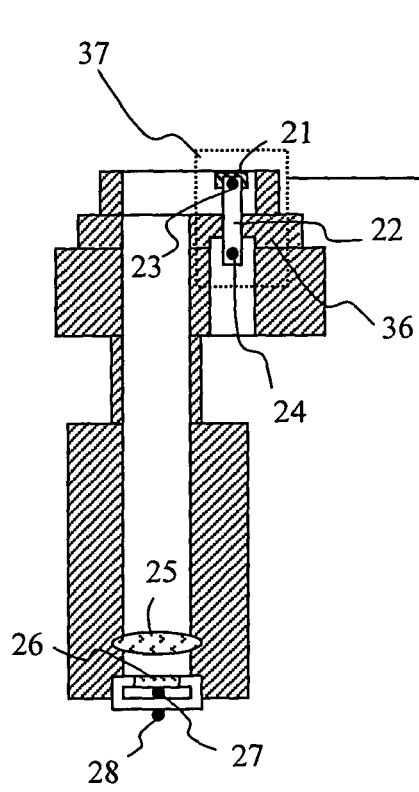
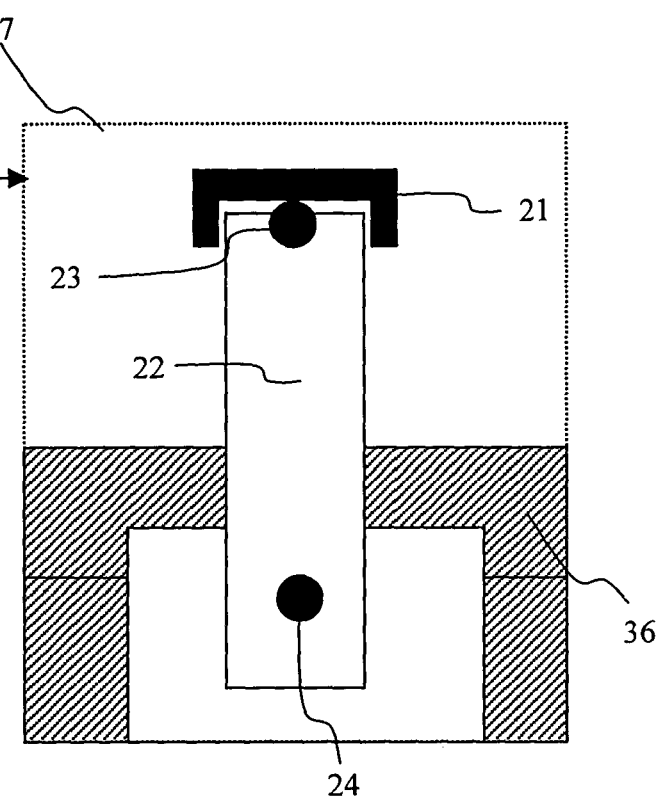

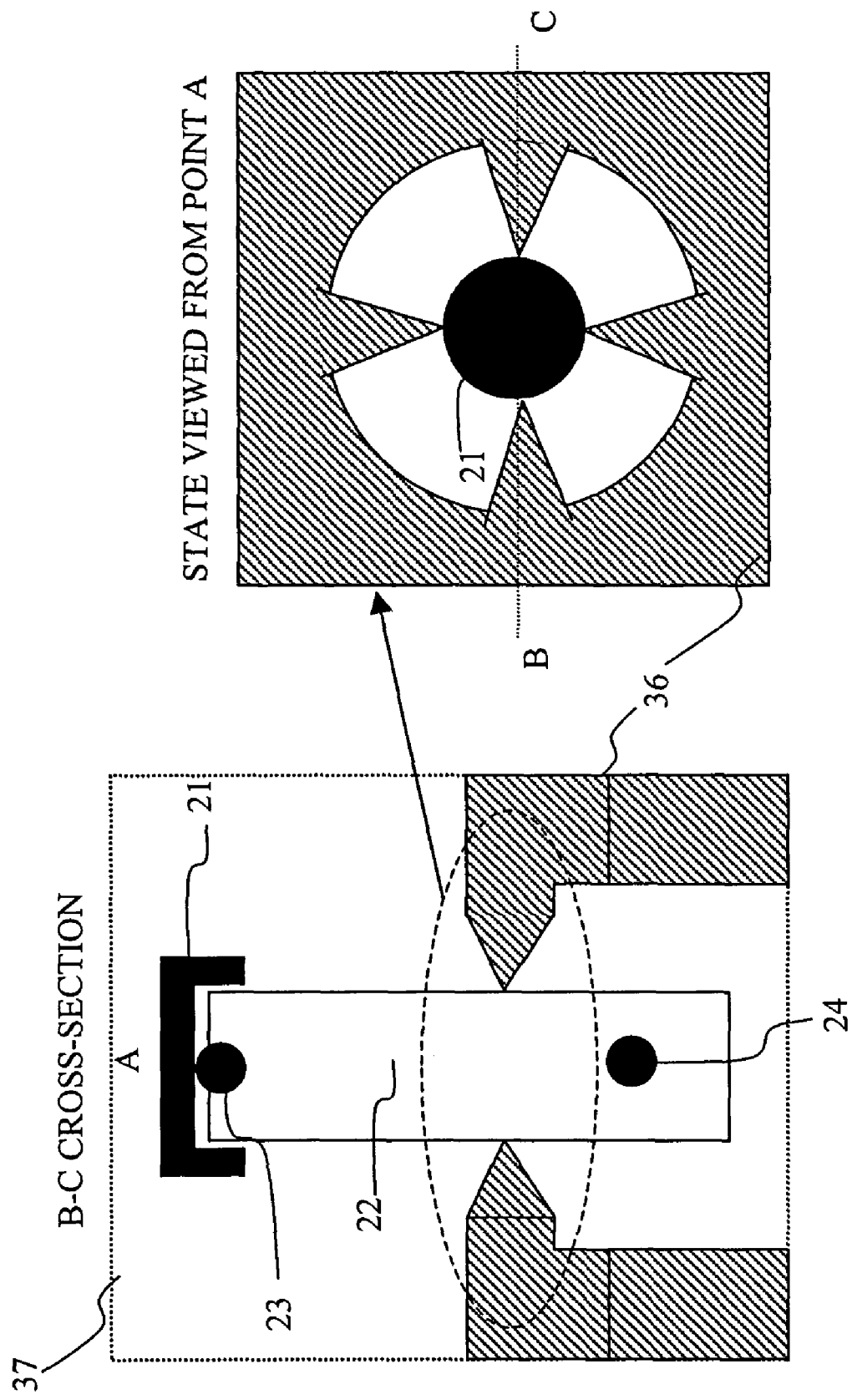

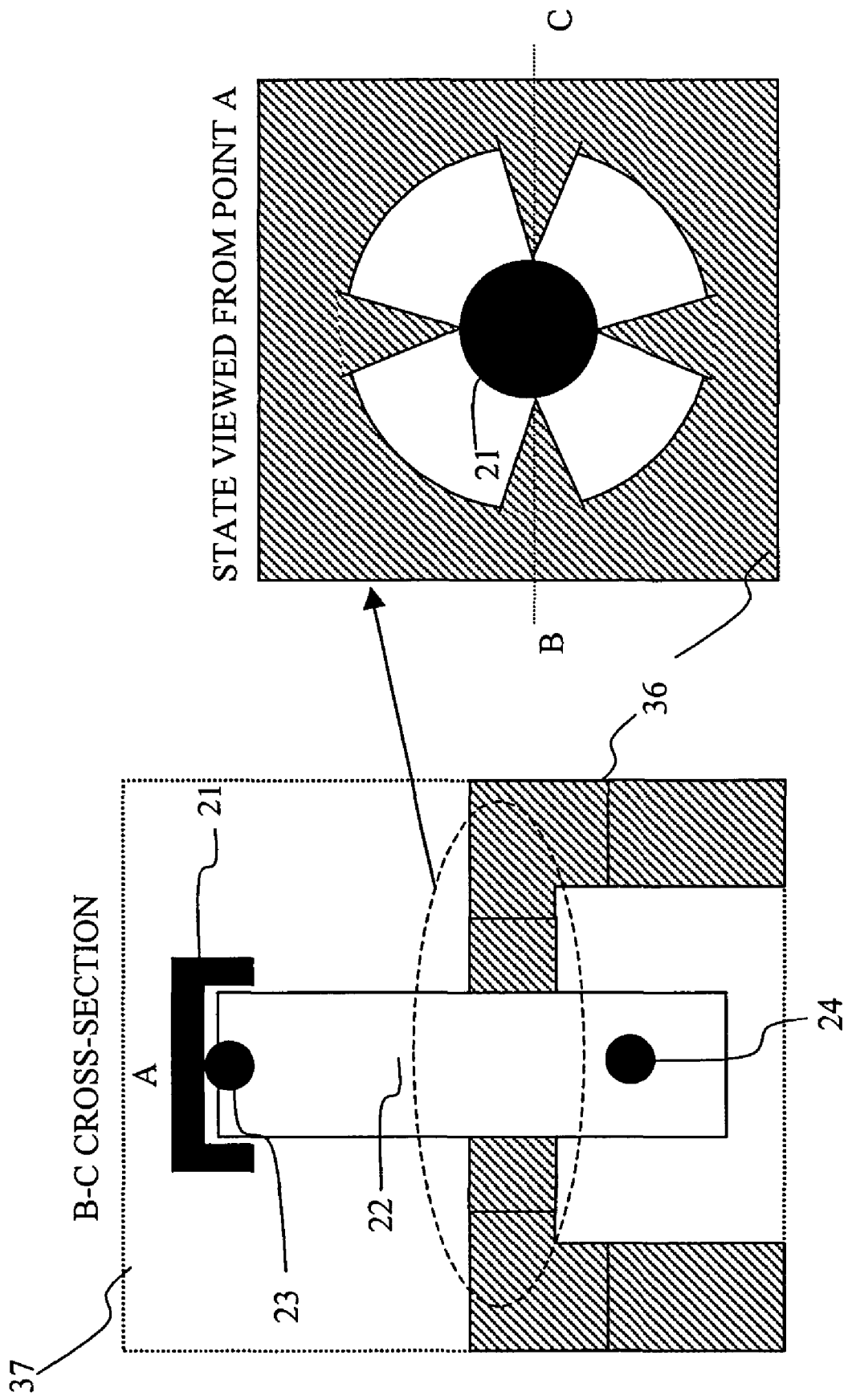

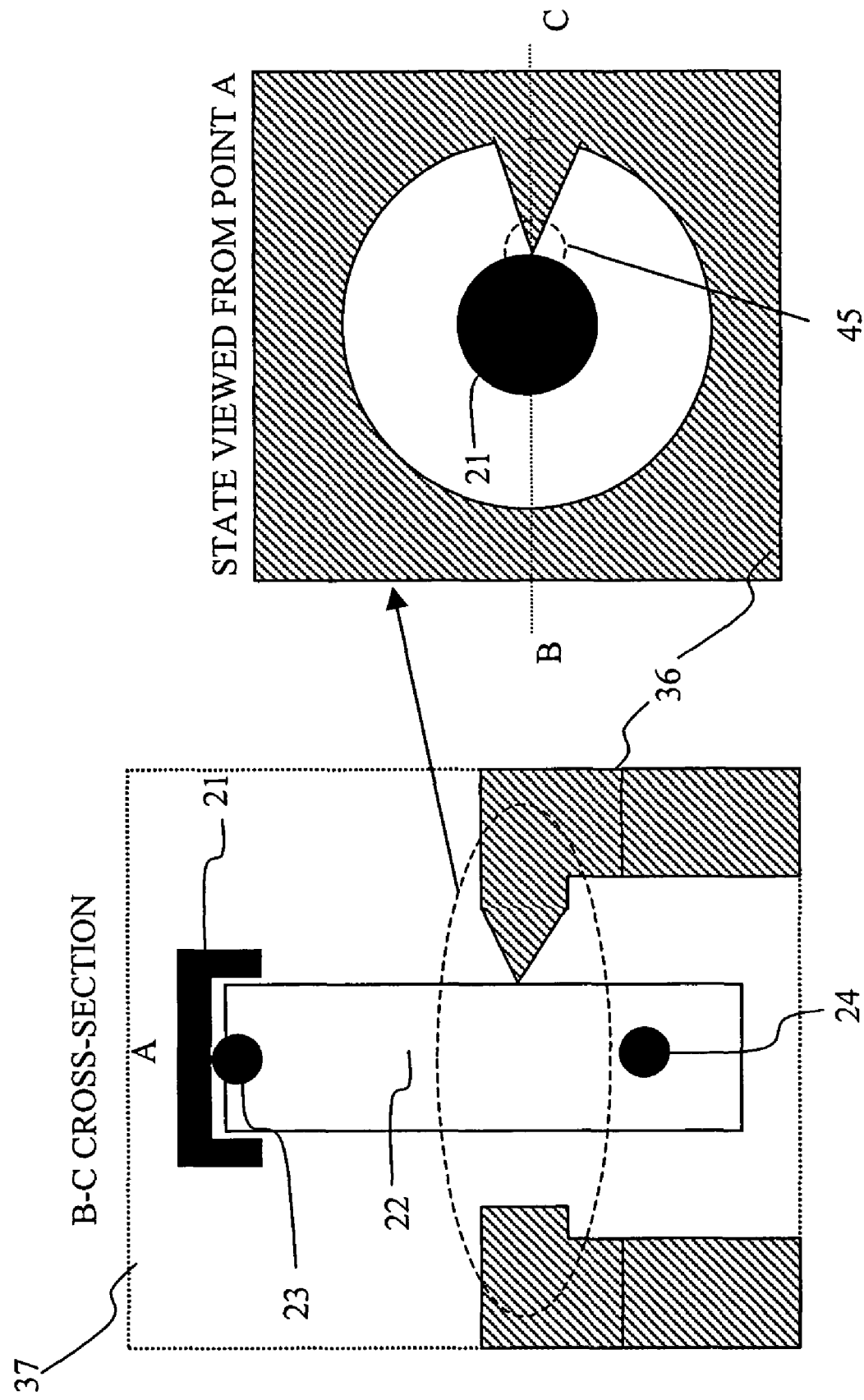

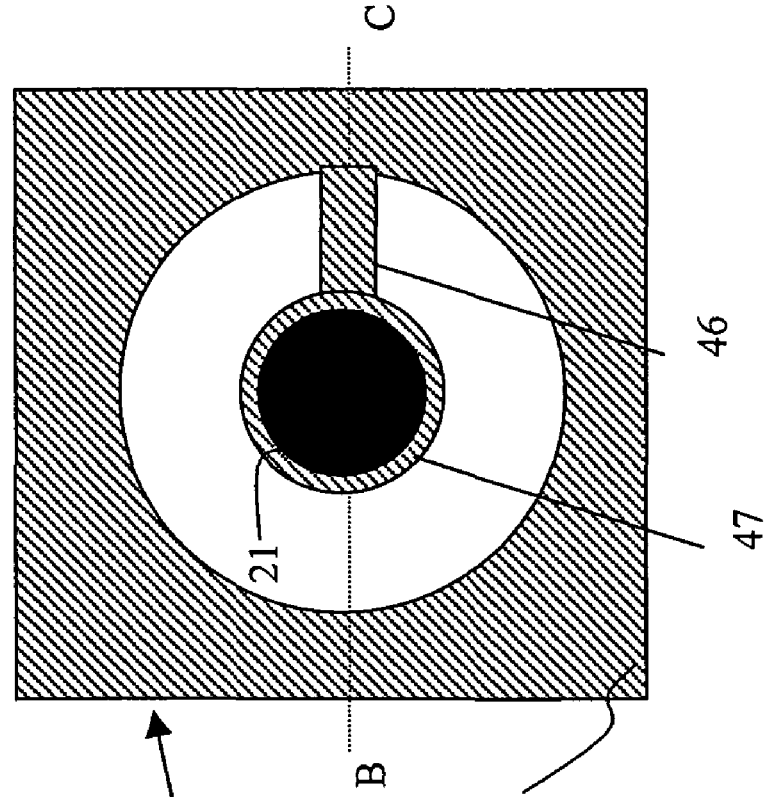
FIG.22(a) B-C CROSS-SECTION
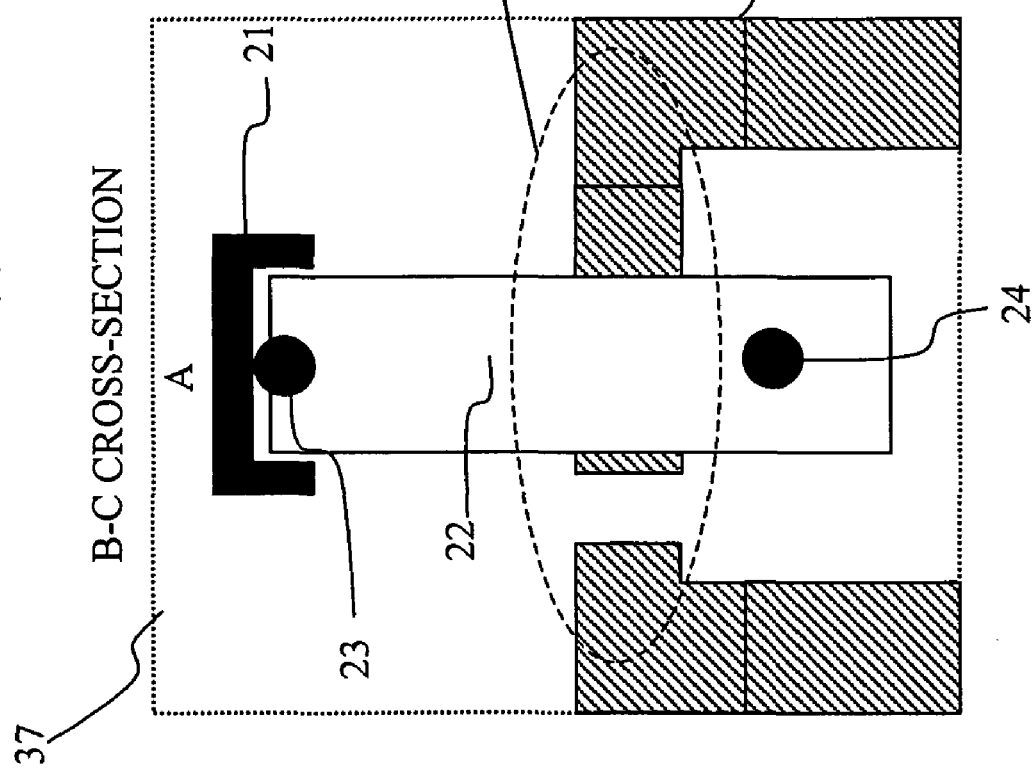
FIG.22(b) STATE VIEWED FROM POINT A

BLOOD SUGAR LEVEL MEASURING APPARATUS

BACKGROUND OF THE INVENTION

1. Field of the Invention

The present invention relates to a method and apparatus for non-invasively measuring glucose concentration in a living body without blood sampling.

2. Background Art

Hilson et al. report facial and sublingual temperature changes in diabetics following intravenous glucose injection (non-patent literature 1). Scott et al. discuss the issue of diabetes mellitus and thermoregulation (non-patent literature 2). Based on such research, Cho et al. suggest a method and apparatus for determining blood glucose concentration by temperature measurement without requiring the collection of a blood sample (patent literature 1 and 2).

Various other attempts have been made to determine glucose concentration without blood sampling. For example, a method has been suggested (patent literature 3) whereby a measurement site is irradiated with near-infrared light of three wavelengths, and the intensity of transmitted light as well as the temperature of the living body is detected. Then, representative values of the second-order differentiated values of absorbance are calculated, and the representative values are corrected in accordance with the difference of the living body temperature from a predetermined reference temperature. The blood sugar level corresponding to the thus corrected representative values is then determined. An apparatus is also provided (patent literature 4) whereby a measurement site is heated or cooled while monitoring the living body temperature. The degree of attenuation of light based on light irradiation is measured at the moment of temperature change so that the glucose concentration responsible for the temperature-dependency of the degree of light attenuation can be measured. Further, an apparatus is reported (patent literature 5) whereby an output ratio between reference light and the light transmitted by an irradiated sample is taken, and then the glucose concentration is calculated by a linear expression of the logarithm of the output ratio and the living body temperature.

(Non-patent literature 1)
R. M. Hilson and T. D. R. Hockaday, "Facial and sublingual temperature changes following intravenous glucose injection in diabetics," Diabete & Metabolisme, 8, pp. 15–19: 1982

(Non-patent literature 2)
A. R. Scott, T. Bennett, I. A. MacDonald, "Diabetes mellitus and thermoregulation," Can. J. Physiol. Pharmacol., 65, pp. 1365–1376: 1987

(Patent Literature 1)
U.S. Pat. No. 5,924,996
(Patent Literature 2)
U.S. Pat. No. 5,795,305
(Patent Literature 3)
JP Patent Publication (Kokai) No. 2000-258343 A
(Patent Literature 4)
JP Patent Publication (Kokai) No. 10-33512 A (1998)
(Patent Literature 5)
JP Patent Publication (Kokai) No. 10-108857 A (1998)

Glucose (blood sugar) in the blood is used for glucose oxidation reaction in cells to produce necessary energy for the maintenance of living bodies. In the basal metabolism state, in particular, most of the produced energy is converted into heat energy for the maintenance of body temperature. Thus, it can be expected that there is some relationship between blood glucose concentration and body temperature. However, as is evident from the way sicknesses cause fever, the body temperature also varies due to factors other than blood glucose concentration.

While methods have been proposed to determine blood glucose concentration by temperature measurement without blood sampling, they lack sufficient accuracy.

SUMMARY OF THE INVENTION

It is the object of the invention to provide a method and apparatus for determining blood glucose concentration with high accuracy based on temperature data of subjects without blood sampling.

Blood sugar is delivered to the cells in the entire human body via the blood vessel system, particularly the capillary blood vessels. In the human body, complex metabolic pathways exist. Glucose oxidation is a reaction in which, fundamentally, blood sugar reacts with oxygen to produce water, carbon dioxide, and energy. Oxygen herein refers to the oxygen delivered to the cells via blood. The volume of oxygen supply is determined by the blood hemoglobin concentration, the hemoglobin oxygen saturation, and the volume of blood flow. On the other hand, the heat produced in the body by glucose oxidation is dissipated from the body by convection, heat radiation, conduction, and so on. On the assumption that the body temperature is determined by the balance between the amount of energy produced in the body by glucose burning, namely heat production, and heat dissipation such as mentioned above, we set up the following model:

(1) The amount of heat production and the amount of heat dissipation are considered equal.
(2) The amount of heat production is a function of the blood glucose concentration and the volume of oxygen supply.
(3) The volume of oxygen supply is determined by the blood hemoglobin concentration, the blood hemoglobin oxygen saturation, and the volume of blood flow in the capillary blood vessels.
(4) The amount of heat dissipation is mainly determined by heat convection and heat radiation.

According to this model, we achieved the present invention after realizing that blood sugar levels can be accurately determined on the basis of the results of measuring the temperature of the body surface and measuring parameters relating to the blood oxygen concentration and the blood flow volume. The parameters can be measured from a part of the human body, such as the fingertip. The parameters relating to convection and radiation can be determined by carrying out thermal measurements on the fingertip. The parameters relating to the blood hemoglobin concentration and the blood hemoglobin oxygen saturation can be determined by spectroscopically measuring the blood hemoglobin and then finding the ratio between the hemoglobin bound with oxygen and the hemoglobin not bound with oxygen. The parameter relating to the volume of blood flow can be determined by measuring the amount of heat transfer from the skin.

It is considered that the heat measurement is affected by various factors such as ambient temperatures, and thus it is necessary to overcome these factors to maintain sufficient accuracy.

In addition, a measurement site for heat measurement, whose temperature is changed by contact with the heat source should satisfy that: the site is formed of a substance, physical properties of which, such as heat capacity, are clarified; the shape of its peripheral configuration is grasped; and the site has a configuration such that it is able to eliminate as much thermal influence except for the heat source as possible. In other words, the measurement site for heat measurement is required to be thermally insulated from the peripheral configuration so that it is disposed not to receive thermal influence therefrom.

In one aspect, the invention provides a blood sugar level measuring apparatus comprising:

a heat amount measuring unit for measuring a plurality of temperatures derived from a body surface in order to obtain information used for calculating the amount of convective heat transfer and the amount of radiation heat transfer concerning the dissipation of heat from the body surface;

an oxygen volume measuring unit for obtaining information concerning the volume of blood oxygen;

a storage unit for storing the relationships between individual parameters corresponding to the multiple temperatures and blood oxygen volume and blood sugar levels;

a computing unit for converting the measurement values provided by the heat amount measuring unit and the oxygen volume measuring unit into parameters, and computing a blood sugar level by applying the parameters to the relationships stored in the storage unit; and a display unit for displaying the blood sugar level computed by the computing unit, wherein the oxygen volume measuring unit comprises a blood flow volume measuring unit for obtaining information concerning the volume of blood flow and a heat transfer prevention means for preventing heat transfer to the blood flow volume measuring unit from the vicinity thereof.

In another aspect, the invention provides a blood sugar level measuring apparatus comprising:

a temperature measuring unit for measuring a plurality of temperatures from a body surface;

a blood flow volume measuring unit for obtaining information concerning the volume of blood flow based on the results of measurement by the temperature measuring unit;

an oxygen volume measuring unit for determining the volume of blood oxygen based on the result of measurement by the blood flow volume measuring unit;

a storage unit for storing the relationships between individual parameters corresponding to the multiple temperatures, the volume of blood oxygen and the volume of blood flow, and blood sugar levels;

a computing unit for converting the measurement values provided by the temperature measuring unit, the blood flow volume measuring unit and the oxygen volume measuring unit into parameters, and then applying the parameters to the relationships stored in the storage unit in order to compute a blood sugar level; and a display unit for displaying the blood sugar level computed by the computing unit, wherein the blood flow volume measuring unit has a heat transfer prevention means for preventing heat transfer to the blood flow volume measuring unit from the vicinity thereof.

In yet another aspect, the invention provides a blood sugar level measuring apparatus comprising:

an ambient temperature measuring unit for measuring the ambient temperature;

a body-surface contact unit to be brought into contact with a body surface;

a radiation heat detector for measuring the radiation heat from the body surface;

a heat-conducting member disposed in contact with the body-surface contact unit;

a heat insulator disposed adjacent the heat-conducting member;

a contact part for covering an open end of the heat-conducting member in contact with the body-surface contact unit;

an adjacent temperature detector for detecting the temperature of the contact part;

an indirect temperature detector disposed adjacent the heat-conducting member and away from the body-surface contact unit for detecting the temperature at a position distanced away from the body-surface contact unit;

a light source for irradiating the body-surface contact unit with light of at least two different wavelengths;

a photodetector for detecting the light with which the body surface has been irradiated;

a converting unit for converting the outputs from the adjacent temperature detector, the indirect temperature detector, the ambient temperature measuring unit, the radiation heat detector, and the photodetector into individual parameters;

a storage unit for storing the relationships between the parameters and blood sugar levels;

a computing unit for computing a blood sugar level by applying the individual outputs to the relationships stored in the storage unit; and a display unit for displaying the blood sugar level produced by the computing unit, wherein the blood flow volume measuring unit has a heat transfer prevention means for preventing heat transfer to the blood flow volume measuring unit from the vicinity thereof.

In these apparatuses, the heat transfer prevention means is an insulation configuration or a configuration for heat conductivity reduction, such as an insulator or an end portion of the supporting column member for mounting the blood flow volume measuring unit.

In yet another aspect, the invention provides a blood sugar level measuring apparatus comprising:

an ambient temperature measuring unit for measuring the ambient temperature;

a body-surface contact unit to be brought into contact with a body surface;

a radiation heat detector for measuring the radiation heat from the body surface;

a heat-conducting member disposed in contact with the body-surface contact unit;

a supporting column member which supports the heat-conducting member and has a smaller diameter at a position adjacent to the heat-conducting member than the maximum diameter of the supporting column member;

a contact part for covering an open end of the heat-conducting member adjacent to the body-surface contact unit;

an adjacent temperature detector for detecting the temperature of the contact part;

an indirect temperature detector disposed adjacent the heat-conducting member and away from the body-surface contact unit for detecting the temperature at a position distanced away from the body-surface contact unit;

a light source for irradiating the body-surface contact unit with light of at least two different wavelengths;

a photodetector for detecting the light with which the body surface has been irradiated;

a converting unit for converting the outputs of the adjacent temperature detector, the indirect temperature detector, the ambient temperature measuring unit, the radiation heat detector, and the photodetector into individual parameters;

a storage unit for storing the relationships between parameters and blood sugar levels;

a computing unit for computing a blood sugar level by applying the individual outputs to the relationships stored in the storage unit; and a display unit for displaying the blood sugar level produced from the computing unit.

In another aspect, the invention provides a blood sugar level measuring apparatus comprising a heat transfer amount measuring unit, the heat transfer amount measuring unit comprising:

a contact part to be brought into contact with a body surface;

a heat-conducting member disposed in contact with the contact part; and an indirect temperature detector disposed adjacent the heat-conducting member and away from the body-surface contact unit for detecting the temperature at a position distanced away from the body-surface contact unit, wherein the heat transfer amount measuring unit is configured so that it is thermally insulated from other portions constituting the blood sugar level measuring apparatus or so that the heat conductivity between the heat transfer amount measuring unit and the other portions constituting the blood sugar level measuring apparatus is low.

In accordance with the invention, blood sugar levels can be determined non-invasively with an accuracy similar to that according to the conventional invasive methods.

BRIEF DESCRIPTION OF THE DRAWINGS

FIG. 10 shows a detailed configuration of a heat transfer amount measuring unit.

FIG. 19 shows a detailed configuration of a heat transfer amount measuring unit having a heat insulation structure.

FIG. 20 shows a detailed configuration of a heat transfer amount measuring unit having a heat insulation structure.

FIG. 21 shows a detailed configuration of a heat transfer amount measuring unit having a heat insulation structure.

FIG. 22 shows a detailed configuration of a heat transfer amount measuring unit having a heat insulation structure.

DESCRIPTION OF THE PREFERRED EMBODIMENTS

The invention will now be described by way of preferred embodiments thereof with reference made to the drawings.

Initially, the above-mentioned model will be described in more specific terms. Regarding the amount of heat dissipation, convective heat transfer, which is one of the main causes of heat dissipation, is related to temperature difference between the ambient (room) temperature and the body-surface temperature. The amount of heat dissipation due to radiation, another main cause of dissipation, is proportional to the fourth power of the body-surface temperature according to the Stefan-Boltzmann law. Thus, it can be seen that the amount of heat dissipation from the human body is related to the room temperature and the body-surface temperature. Another major factor related to the amount of heat production, oxygen supply, is expressed as the product of hemoglobin concentration, hemoglobin oxygen saturation, and blood flow volume.

The hemoglobin concentration can be measured by the absorbance at the wavelength at which the molar absorbance coefficient of the oxy-hemoglobin is equal to that of the deoxy-hemoglobin (equal-absorbance wavelength). The hemoglobin oxygen saturation can be measured by measuring the absorbance at the equal-absorbance wavelength and the absorbance of at least one different wavelength at which the ratio between the molar absorbance coefficient of the oxy-hemoglobin and that of the deoxy-hemoglobin is known, and then solving simultaneous equations. Namely, the hemoglobin concentration and the hemoglobin oxygen saturation can be obtained by measuring absorbance of at least two wavelengths.

The rest is the blood flow volume, which can be measured by various methods. One example will be described below.

Figure 1:
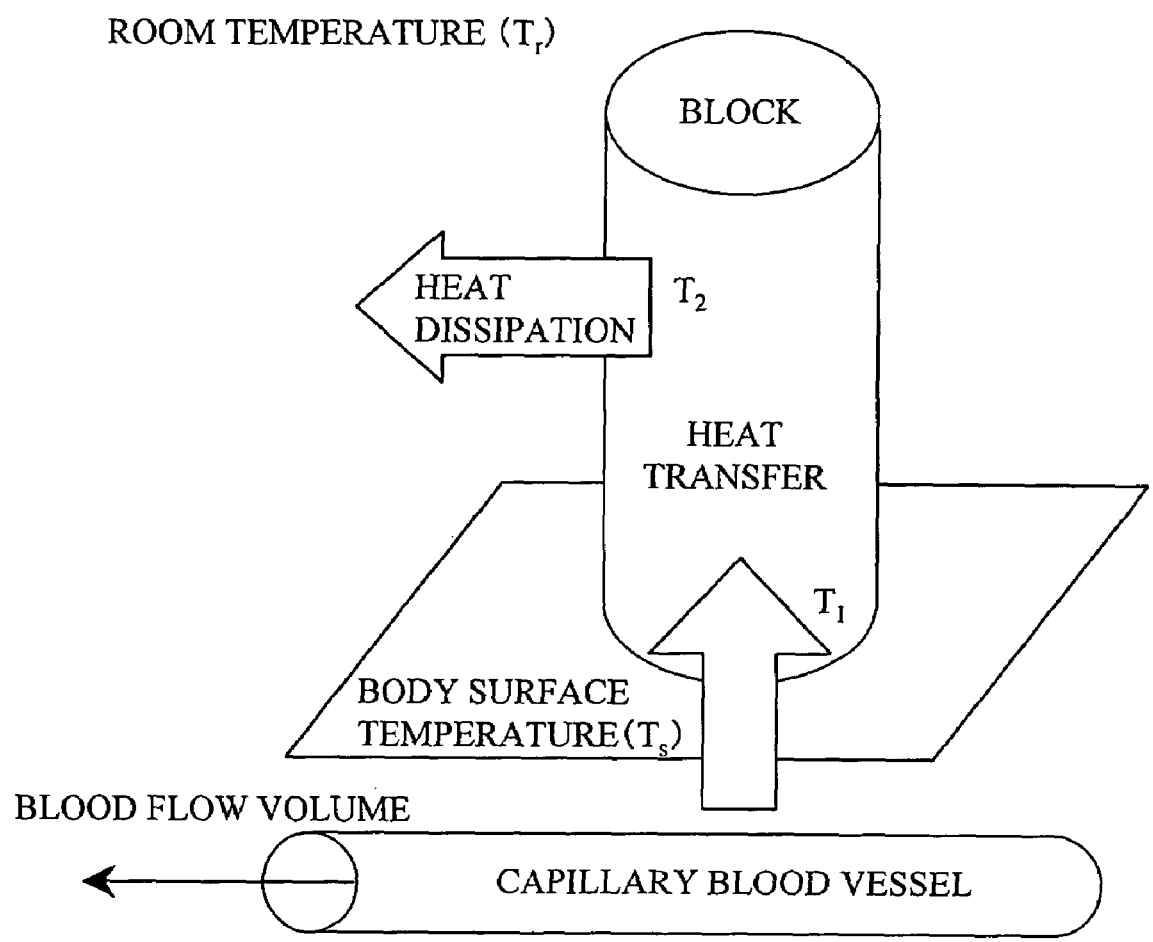
FIG. 1 shows a model of heat transfer from the body surface to a block.

FIG. 1 shows a model for the description of the transfer of heat from the body surface to a solid block having a certain heat capacity when the block is brought into contact with the body surface for a certain time and then separated. The block is made of resin such as plastic or vinyl chloride. (For more detail, it is necessary to mention about the biocompatible material e.g. ABS which has a medical degree. It is required to use such material for medial device generally.)

In the illustrated example, attention will be focused on the chronological variation of the temperature $T_1$ of a portion of the block in contact with the body surface, and the chronological variation of the temperature $T_2$ of a point on the block away from the body surface. The blood flow volume can be estimated by monitoring mainly the chronological variation of the temperature $T_2$ (of a point on the spatially separated block). The details will be described later.

Before the block comes into contact with the body surface, the temperatures $T_1$ and $T_2$ at the two points of the block are equal to the room temperature $T_r$. When a body-surface temperature $T_1$ is higher than the room temperature $T_r$, the temperature $T_1$ swiftly rises due to the transfer of heat from the skin as the block contacts the body surface, and it approaches the body-surface temperature $T_s$. On the other hand, the temperature $T_2$ is less than the temperature $T_1$ as the heat conducted through the block is dissipated from the block surface, and it rises more gradually than the temperature $T_1$. The chronological variation of the temperatures $T_1$ and $T_2$ depends on the amount of heat transferred from the body surface to the block, which in turn depends on the blood flow volume in the capillary blood vessels under the skin. If the capillary blood vessels are regarded as a heat exchanger, the heat transfer coefficient from the capillary blood vessels to the surrounding cell tissues is given as a function of the blood flow volume. Accordingly, by monitoring the temperature changes in the $T_1$ and $T_2$ chronologically, and thus measuring the amount of heat transfer from the body surface to the block, the amount of heat transfer from the capillary blood vessels to the cell tissues can be estimated, so that the blood flow volume can be estimated.

The relationship between the temperature distribution and the amount of heat is given by the following equation on the basis of Fourier's law:

$$q = -\lambda(\delta T/\delta n)$$

Here, q (unit: $W/m^2$) represents heat flux expressing the heat amount passing through a unit of cross-sectional area per unit of time. $\lambda$ (W/mK) represents heat conductivity of the substance, T (K) represents a temperature on the surface or the inside of a substance, and n represents a coordinate of the direction, for which the heat flux is sought.

Fourier's law given by the above equation indicates that when there is temperature distribution inside a substance, the heat flow occurs along the direction of the temperature distribution, that is, from a high temperature to a low temperature vertically to an isotherm of the inside of the substance. It also indicates that the amount of heat flux occurring between two points inside a substance is proportional to the temperature difference between these two points. Such proportional coefficient is defined as heat conductivity (W/mK).

Therefore, when physical properties such as the heat conductivity of a substance or the dimensional size such as a volume V ($m^3$) or a surface area F ($m^2$) are clarified and the temperature distribution inside (or on the surface of) the substance is obtained, it is known that heat flux can be calculated from the results of the temperature measurement and the heat conductivity of the substance.

Furthermore, when the cross-sectional area with respect to the flow direction is known, it is possible to obtain the amount of heat flowing into or out from the substance per unit of time by multiplying the calculated heat flux by the cross-sectional area of the substance. In addition, the total amount of heat transferred from the heat source to the substance while the substance is in contact with the heat source can be calculated by multiplying the heat amount by the time during which the substance and the heat source are in contact.

However, heat supplied from the heat source to a substance in contact therewith comprises a component which is lost due to heat release (radiation) from the substance surface, in addition to a component which forms the temperature distribution by heat conduction inside the substance. This is a non-negligible factor when estimating the total heat amount supplied from the heat source.

The heat flux of the heat amount lost by the radiation (heat flux of radiation: $q_r$ ($W/m^2$)) can be calculated as indicated by the equation below by obtaining chronological temperature variations of the substance in contact with the heat source together with the ambient temperature (room temperature represented by Tr) when the heat conductivity, density $\rho$ ($kg/m^3$), specific heat c (J/kgK), volume V ($m^3$), surface area F ($m^2$) and the like of a substance are known. Here, a one-dimensional coordinate system will be used for simple explanation.

Taking a point in contact with the heat source as an origin, a measurement point is set at a position at a distance "x" from the origin. The value measured at the measurement point is expressed as T(K). The heat amount ($W/m^2$) released by radiation from the substance surface corresponding to the measurement point is given by the following Stefan-Boltzmann equation.

$$q_r = \epsilon\sigma(T^4 - Tr^4) = \alpha(\delta^2 T/\delta x^2)\rho c V/F - (\delta T/\delta t)\rho c V/F$$

The characters "$\epsilon$" and "$\sigma$" represent emissivity and Stefan-Boltzmann constant, respectively. The characters "T," "t," and "x" represent measured temperature, time, and a coordinate on the one-dimensional coordinate system. The character "$\alpha$" on the right side of the equation represents heat conductivity ($m^2/s$). The product (first term of the right side of the equation) of heat conductivity (physical property) and the value obtained by second-order differentiation of the measured temperature with respect to the position represents the heat flux on the assumption that the total heat amount supplied by heat conduction inside the substance reaches the measurement point "x" and the temperature distribution occurs. In contrast, the second term of the right side of the equation represents the heat flux obtained from actual chronologically measured variations (time differentiation of the measured temperature). The difference between these heat fluxes is the heat flux released to the outside of the substance in the form of radiation.

As described above, the heat amount $Q_{total}$ (W) transferred from the heat source in contact with the substance can be calculated by measuring the temperature distribution of the substance having known physical properties and chronological temperature variations. Namely, the heat amount $Q_{total}$ (W) transferred from the heat source is obtained by multiplying the sum of the heat fluxes obtained from the above Fourier's law and Stefan-Boltzmann equation, by a cross-sectional area of the substance (area in contact with the heat source), as indicated by the following equation.

$$Q_{total} = \{q + q_r\}F$$

Hereafter, the outline of the calculation method will be described by showing temperature measurement waveforms.

Figure 2:
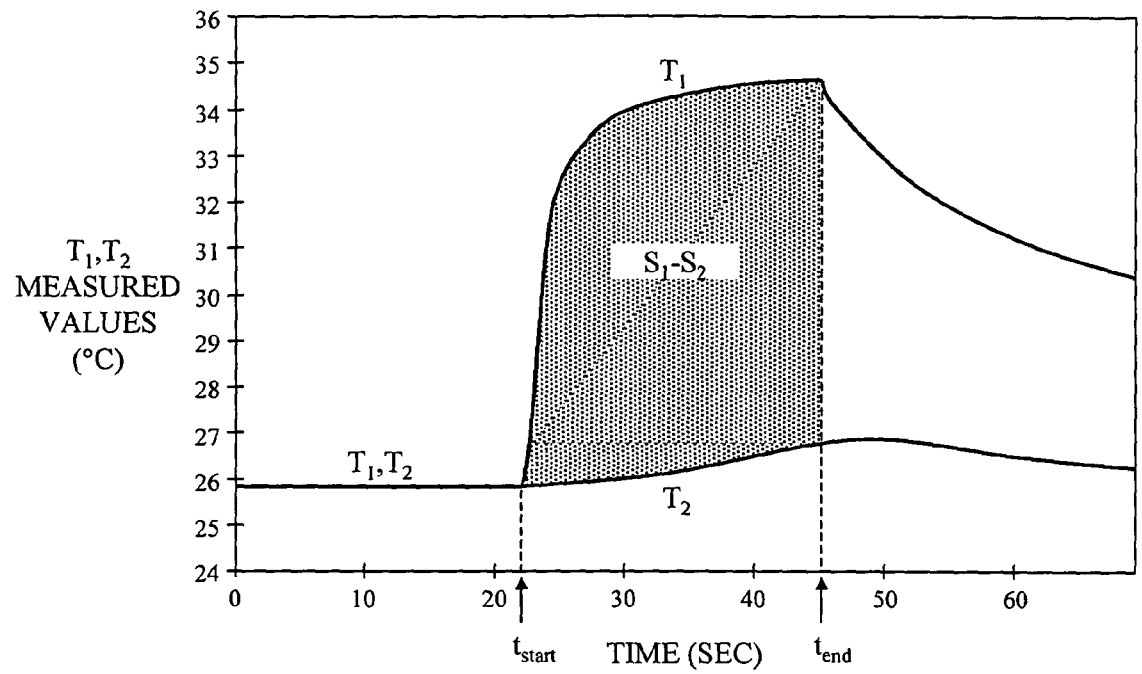
FIG. 2 plots the measurement values of temperatures $T_1$ and $T_2$ as they change with time.

FIG. 2 shows the chronological variation of the measured values of the temperature $T_1$ at the portion of the block in contact with the body surface and the temperature $T_2$ at the position on the block away from the body-surface contact position. As the block comes into contact with the body surface, the $T_1$ measured value swiftly rises, and it gradually drops as the block is brought out of contact.

Figure 3:
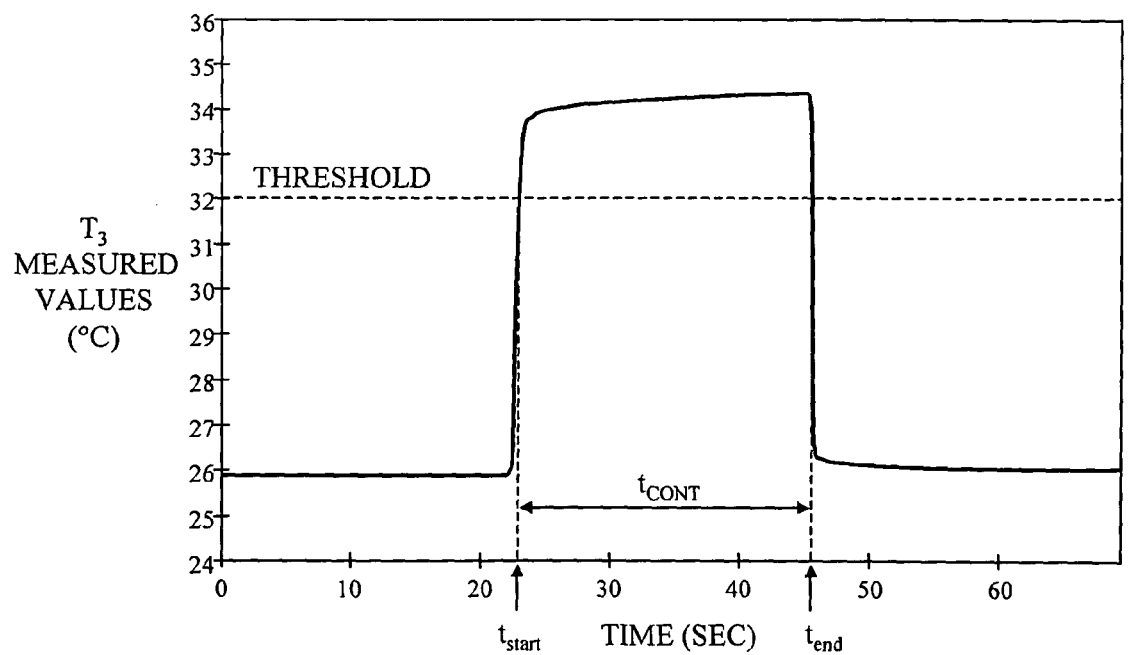
FIG. 3 shows an example of measuring the chronological change in temperature $T_3$.

FIG. 3 shows the chronological variation of the measured value of the temperature $T_3$ measured by a radiation temperature detector. As the detector detects the temperature due to the radiation from the body surface, it is more sensitive to temperature changes than other sensors. Because radiation heat propagates as an electromagnetic wave, it can transmit temperature changes instantaneously. Thus, by locating the radiation temperature detector near where the block contacts the body surface, as shown in FIG. 7 which will be described later, the time of start of contact $t_{start}$ between the block and the body surface, and the time of end of contact $t_{end}$ can be detected by changes in the temperature $T_3$. For example, a temperature threshold value is set as shown in FIG. 3. The contact start time $t_{start}$ is when the temperature threshold value is exceeded. The contact end time tend is when the temperature $T_3$ drops below the threshold. The temperature threshold is set at 32° C., for example.

Then, the $T_1$ measured value between $t_{start}$ and $t_{end}$ is approximated by an S curve, such as a logistic curve. A logistic curve is expressed by the following equation:

$$T = \frac{b}{1 + c \times \exp(-a \times t)} + d$$

where T is temperature, and t is time.

The measured value can be approximated by determining factors a, b, c, and d by the non-linear least-squares method. For the resultant approximate expression, T is integrated between time $t_{start}$ and time $t_{end}$ to obtain a value $S_1$.

Similarly, an integrated value $S_2$ is calculated from the $T_2$ measured value. The smaller $(S_1-S_2)$, the larger the amount of transfer of heat from the finger surface to the position of $T_2$. $(S_1-S_2)$ becomes larger with increasing finger contact time $t_{CONT}$ $(=t_{end}-t_{start})$. Thus, $a_5/(t_{CONT} \times (S_1-S_2))$ is designated as a parameter $X_5$ indicating the volume of blood flow, where $a_5$ is a proportionality coefficient.

Thus, it will be seen that the measured amounts necessary for the determination of blood glucose concentration by the above-described model are the room temperature (ambient temperature), body surface temperature, temperature changes in the block brought into contact with the body surface, the temperature due to radiation from the body surface, and the absorbance of at least two wavelengths.

Figure 4:
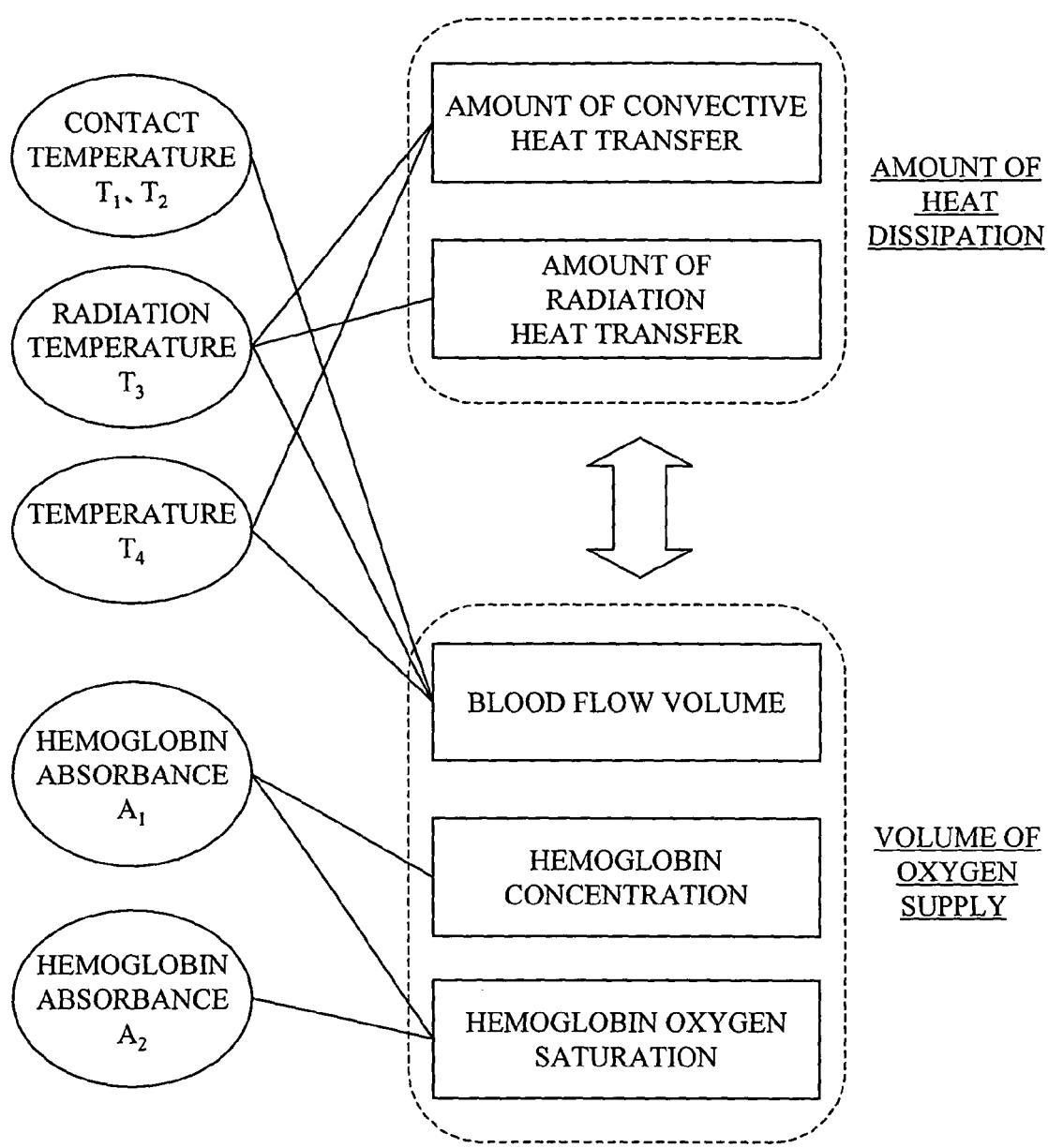
FIG. 4 shows the relationships between measurement values provided by various sensors and the parameters derived therefrom.

FIG. 4 shows the relationships between the measured values provided by various sensors and the parameters derived therefrom. A block is brought into contact with the body surface, and chronological change in two kinds of temperatures $T_1$ $_{and}$ $_{T2}$ are measured by two temperature sensors provided at two locations of the block. A radiation temperature $T_3$ on the body surface and the room temperature $T_4$ are separately measured. Absorbance $A_1$ and $A_2$ are measured at at least two wavelengths related to the absorption of hemoglobin. The temperatures $T_1$, $T_2$, $T_3$, and $T_4$ provide parameters related to the volume of blood flow. The temperature $T_3$ provides a parameter related to the amount of heat transferred by radiation. The temperatures $T_3$ and $T_4$ provide parameters related to the amount of heat transferred by convection. The absorbance $A_1$ provides a parameter related to the hemoglobin concentration. The absorbance $A_1$ and $A_2$ provide parameters related to the hemoglobin oxygen saturation.

Hereafter, an example of apparatus for non-invasively measuring blood sugar levels according to the principle of the invention will be described.

Figure 5:
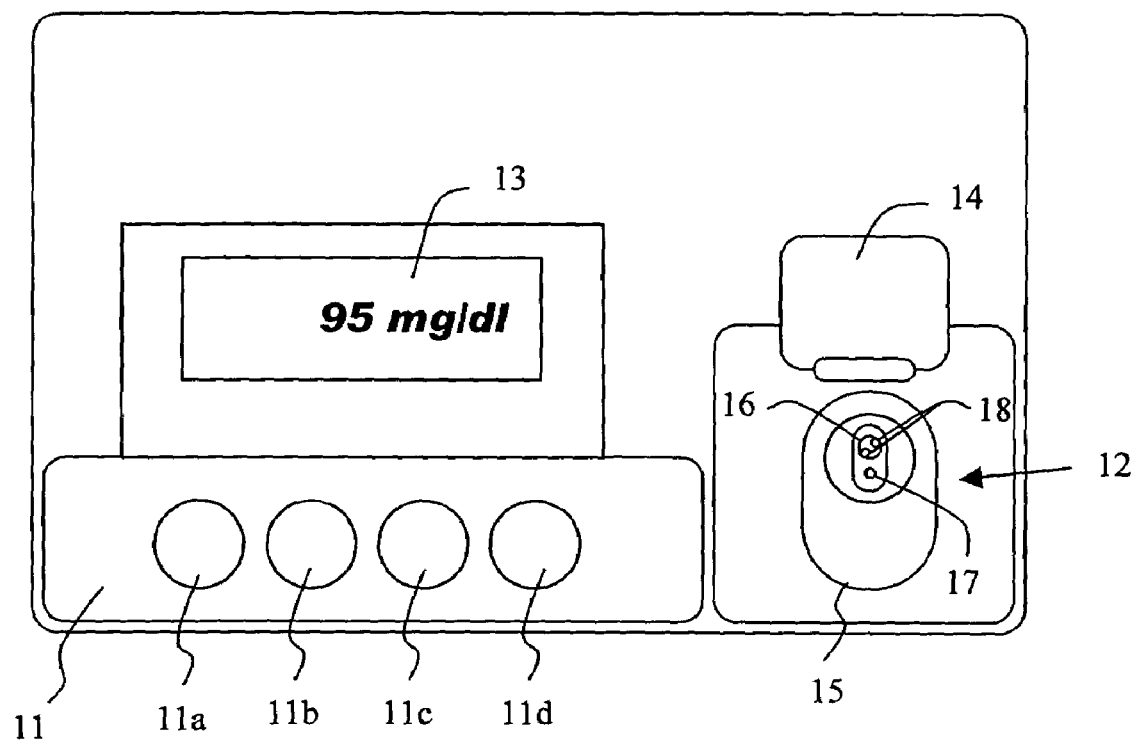
FIG. 5 shows an upper plan view of a non-invasive blood sugar level measuring apparatus according to the present invention.

FIG. 5 shows a top plan view of the non-invasive blood sugar level measuring apparatus according to the invention. While in this example the skin on the ball of the finger tip is used as the body surface, other parts of the body surface may be used.

On the top surface of the apparatus are provided an operation unit 11, a measuring unit 12 where the finger to be measured is to be placed, and a display unit 13 for displaying the state of the apparatus, measured values, and so on. The operation unit 11 includes four push buttons 11a to 11d for operating the apparatus. The measuring unit 12 has a cover 14 which, when opened (as shown), reveals a finger rest 15 with an oval periphery. The finger rest 15 accommodates an opening end 16 of a radiation temperature sensor, a contact temperature sensor 17, and an optical sensor unit 18.

Figure 6:
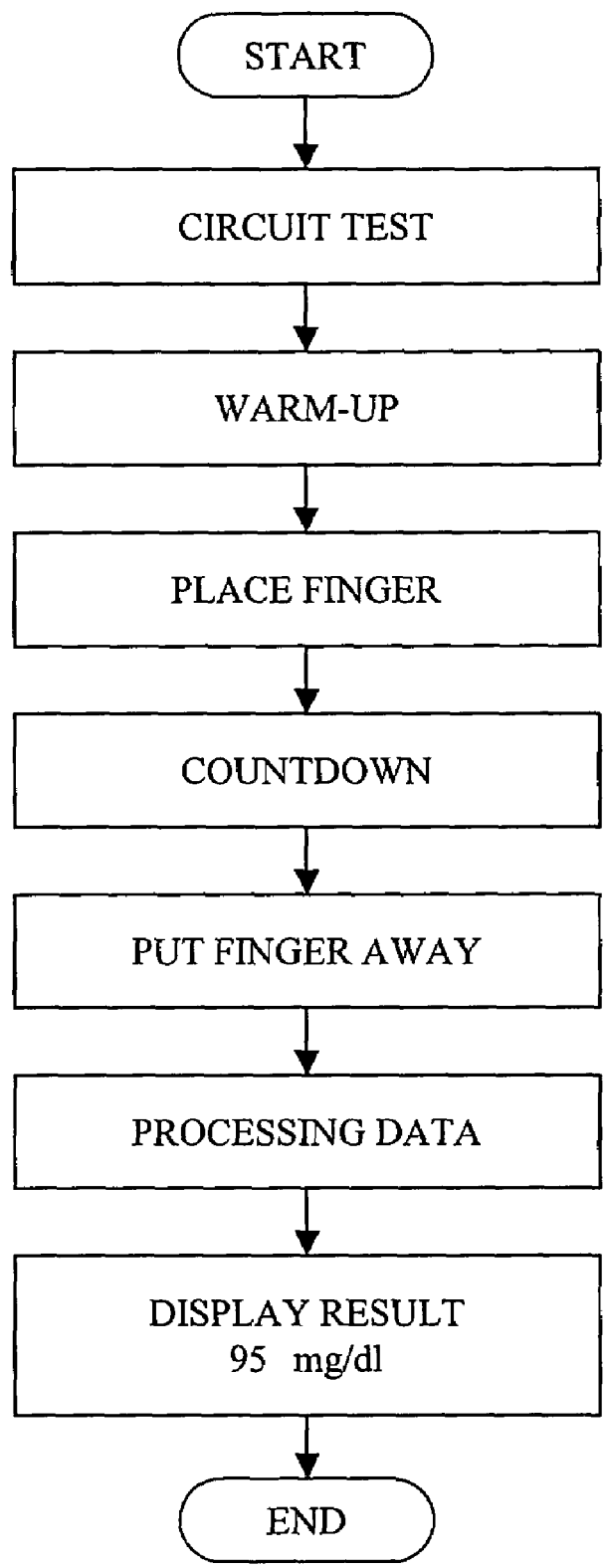
FIG. 6 shows the operating procedure for the apparatus.

FIG. 6 shows the procedure for operating the apparatus. As one of the buttons on the operation unit is depressed and the apparatus is turned on, an indication "Warming up" is displayed on the LCD display while the electronic circuits in the apparatus are being warmed up. At the same time, a check program is activated to automatically check the electric circuits. As the warm-up phase is over, an indication "Place your finger" appears on the LCD display. As the user places his or her finger on the finger rest, the LCD display begins counting down. When the countdown is over, an indication "Put your finger away" appears on the LCD display. As the user follows the instruction, the LCD display indicates "Processing data." Thereafter, the display shows the blood sugar level, which is then stored in an IC card together with the date and time. As the user took notes of the displayed blood sugar level, he or she pushes another button on the operation unit. About one minute later, the apparatus displays a message "Place your finger" on the LCD display, thus indicating that the apparatus is ready for the next cycle of measurement.

Figure 7A:
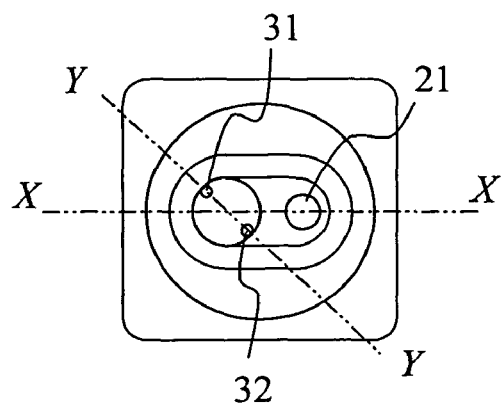
FIG. 7 shows the measuring unit in detail.
Figure 7B:
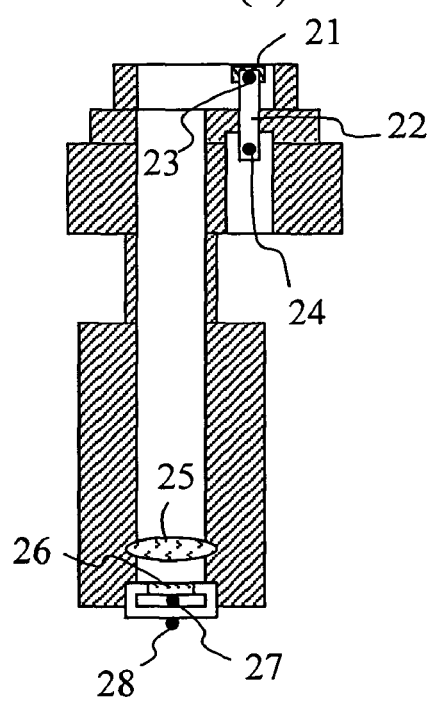

FIG. 7 shows the measuring unit in detail. FIG. 7(a) is a top plan view, (b) is a cross section along line X—X of (a), and (c) is a cross section along line Y—Y of (a).

First, the process of measuring temperature by the non-invasive blood sugar level measuring apparatus according to the invention will be described. In the portion of the measuring unit where the object of measurement (ball of the finger) is to come into contact, a thin plate 21 of a highly heat-conductive material, such as gold, is placed. A bar-shaped heat-conducting member 22 made of material such as polyvinylchloride whose heat conductivity is lower than that of the plate 21 is thermally connected to the plate 21 and extends into the apparatus. The temperature sensors include a thermistor 23 for measuring the temperature of the plate 21 and acting as an adjacent temperature detector with respect to the measured object. There is also a thermistor 24 for measuring the temperature of the heat-conducting member away from the plate 21 by a certain distance and acting as an indirect temperature detector with respect to the measured object. The plate 21, heat-conducting member 22, and thermistors 23 and 24 constitute a heat transfer amount measuring unit. As described above, in the calculation process of the heat amount according to the measurement method of the present invention, it is important that physical properties of a contact part as an object of temperature measurement in a measuring unit where a finger as the measured object is placed, the shape of peripheral structure of the contact part, and the like are definite. Further, a certain amount of heat supplied from a heat source such as a finger is externally released and consumed, in addition to heat used to form the temperature distribution inside the contact part (particularly the plate 21) and the heat-conducting member 22 and heat lost from the contact part as radiation heat. Furthermore, there is a possibility that heat is supplied from a source other than the heat source, that is, the measured object. In such cases, heat to be measured is not measured, or heat that should not be measured is measured. As a result, a measurement error is caused, and thus there is a possibility that an error would occur in calculating a final blood glucose concentration.

For this reason, heat exchange is carried out through contact with the heat source, and the heat transfer amount measuring unit for measuring the temperature of the heat source is thermally insulated from the other parts constituting the blood sugar measuring apparatus. Alternatively, the heat conduction between the heat transfer amount measuring unit and the other constituent parts of the blood sugar measuring apparatus is inhibited, resulting in a structure having lowered heat conductivity. As a result of this, measurement errors which may occur will be reduced, so that the blood glucose concentration is obtained with improved accuracy. In addition to this structure, the apparatus is configured so as to strengthen the thermal connection by employing a structure such that: the plate 21 is formed of gold or a metal having a high heat conductivity equal to gold; and the thermistors 23 and 24 are connected to the heat-conducting member 22 with an adhesive having a high heat conductivity, or implanted in the heat-conducting member 22.

FIG. 10 shows a detailed view (a) of the measuring unit and a detailed, magnified view (b) of peripheral structure 37 of the heat transfer amount measuring unit thereof. As shown in FIG. 10(b), the heat transfer amount measuring unit has a structure such that the plate 21 and thermistors 23 and 24 are mounted on the bar-shaped (herein, for example, a round bar) heat-conducting member 22, and the heat-conducting member 22 is mounted in contact with a supporting column portion 36 constituting the blood sugar level measuring apparatus.

Figure 11:
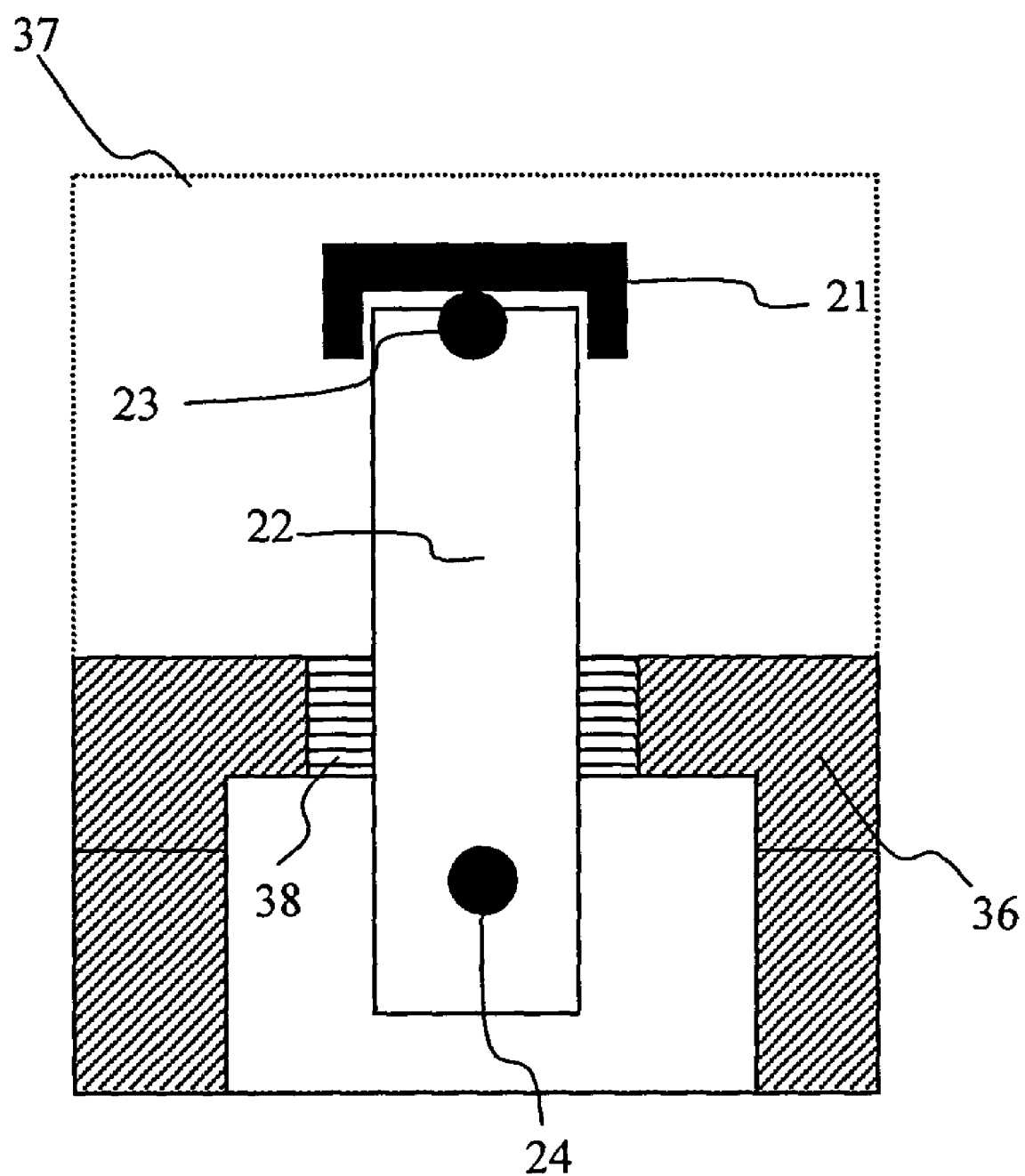
FIG. 11 shows a detailed configuration of a heat transfer amount measuring unit having a heat insulation structure.

FIG. 11 shows an embodiment wherein a heat insulation structure or a structure for reducing heat conductivity is applied to the heat transfer amount measuring unit described in FIG. 10(b). In this embodiment, a heat insulator 38 is concentrically disposed with respect to the round bar-shaped heat-conducting member 22 to be mounted on the supporting column portion 36 through the heat insulator. As the heat insulator used herein, fiber materials or foaming materials having voids formed therein, or micro dust layer materials, may be employed. In the case of fiber materials, asbestos, glass wool, or materials having fiber properties similar thereto may be used, and the heat conductivity thereof may be from about 0.0005 W/mK to about 0.002 W/mK. In the case of foaming materials, polyurethane, polystyrene, or materials having properties similar to foaming material may be used, and the heat conductivity thereof may be from about 0.005 W/mK to about 0.02 W/mK. Moreover, in the case of micro dust layer materials, perlite, silica aerogel, or materials having the properties similar to micro dust layer material may be used, and the heat conductivity thereof may be from about 0.0005 W/mK to about 0.009 W/mK. Namely, the materials used as the heat insulator desirably have a heat conductivity from about 0.0005 W/mK to about 0.02 W/mK. The heat conductivity of the portion where such heat insulator is used can be substantially reduced in light of the facts that the heat conductivity of air is approximately 0.025 W/mK and that the heat conductivity is several hundred mW/mK when a resin material such as a plastic is used as a material for main portions of the apparatus except portions replaceable with a heat insulator and various detectors. As a result, the heat exchange between the heat-conducting member 22 and the supporting column portion 36 can be substantially reduced. While the heat insulator is practically in contact with the heat-conducting member 22 and the supporting column portion 36, the heat insulator used herein has a lower heat conductivity than either of these items.

Figure 18A:
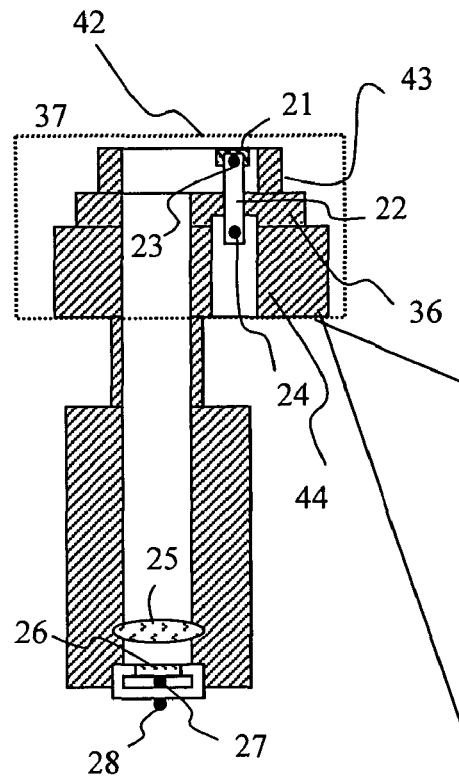
FIG. 18 shows a detailed configuration of a heat transfer amount measuring unit having a heat insulation structure.
Figure 18B:
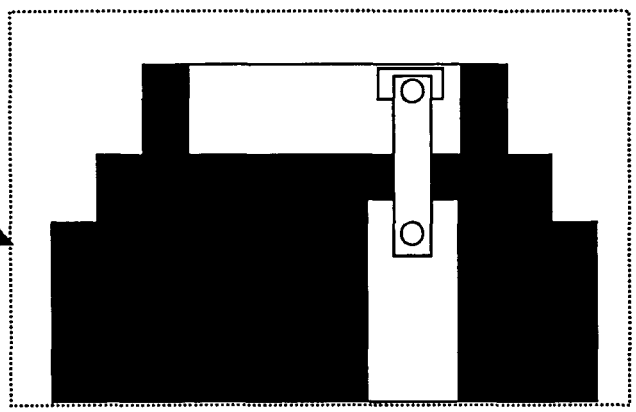
Figure 18C:
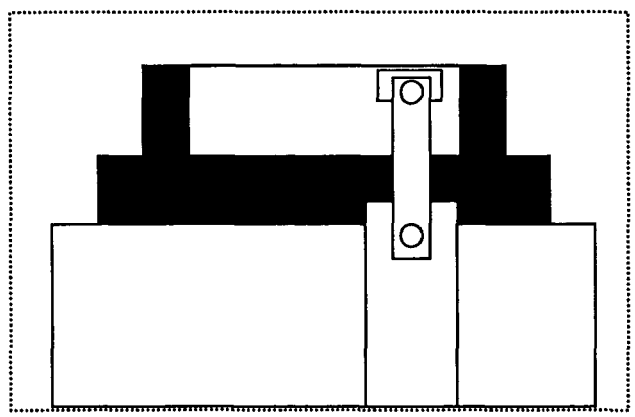

The structure wherein the heat insulator is inserted in a portion of the apparatus is described above. However, the shape as shown in FIG. 18 is available wherein at least a portion of an upper supporting column member 43 or a lower supporting column member 44 placed surrounding the supporting column portion 36 and the heat-conducting member 22 is formed of an insulating material, and the heat-conducting member 22 is mounted on these members. FIG. 18 shows a detailed view (a) of the measuring unit, a detailed, magnified view (b) of one embodiment of the heat transfer amount measuring unit and a peripheral portion 42 thereof, and a detailed, magnified view (c) of another embodiment of the heat transfer amount measuring unit and the peripheral portion 42 thereof. In the figure, portions formed of the insulating material are colored black. Here, the properties of the insulating material are the same as above. While the upper supporting column member 43, the supporting column portion 36, and the lower supporting column member 44 are all formed of the insulating material in FIG. 18(b), the upper supporting column member 43 and the supporting column portion 36 are formed of the insulating material in FIG. 18(c). In addition, the side portion of the heat-conducting member 22 may be covered with the insulating material. Such structure enables a larger reduction in the heat exchange from the heat-conducting member 22 to the other constituent portions of the apparatus adjacent to the heat-conducting member 22 through the insulating material portion in the same manner the structure of FIG. 11.

As described above, the total heat amount to be transferred between substances or within a substance is a value obtained by multiplying the heat flux (W/m$^2$) defined by the temperature difference and heat conductivity by the contact area F (m$^2$). When an insulator is employed as shown in the figure, the heat conductivity from the heat-conducting member to other constituent portions is reduced to decrease the heat flux. As a result, it is possible to reduce the total heat amount to be transferred from the heat-conducting member to the other constituent portions.

Figure 12:
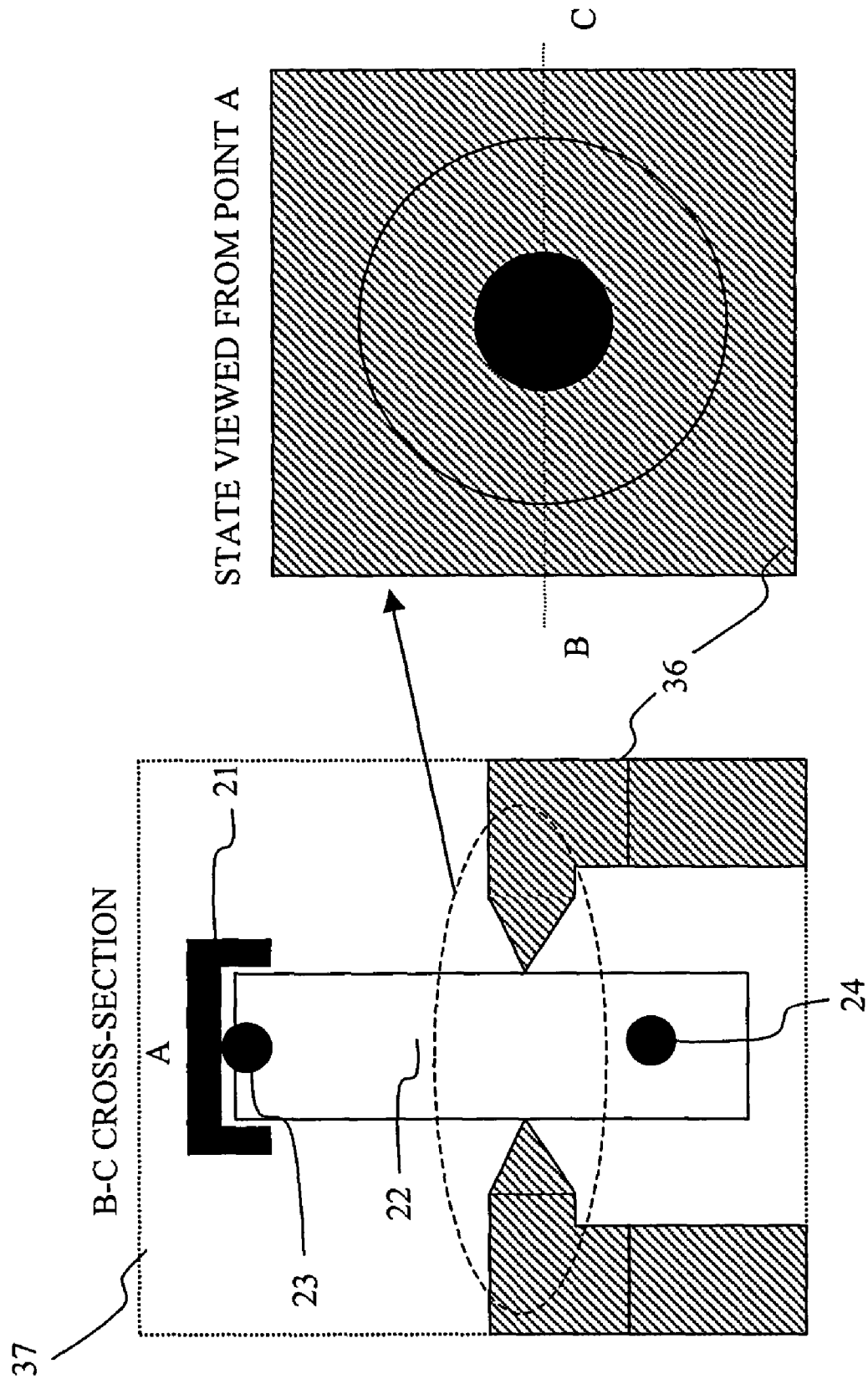
FIG. 12 shows a detailed configuration of a heat transfer amount measuring unit having a heat insulation structure.

FIG. 12 shows an embodiment wherein the cross section of a contact portion of the supporting column portion 36, shown in FIG. 10(b), with the heat-conducting member 22 has a triangular shape so that the supporting column portion 36 has a line contact with the heat-conducting member 22. FIG. 12(a) is a detailed, magnified view of a peripheral structure 37 of the heat transfer amount measuring unit and a cross-section along line B-C of FIG. 12(b). FIG. 12(b) shows a state viewed from point A of FIG. 12(a). As described above, the total heat amount to be transferred between substances or within a substance is obtained by multiplying the heat flux (W/m$^2$) defined by a temperature difference and heat conductivity by a contact area F (m$^2$). According to the present method, the heat flux is not decreased but the contact area is deceased, so consequently the heat to be transferred is reduced.

In addition to the cross-sectional shape as shown in FIG. 12, any of point contact, which is a contact shape formed through point contact, longitudinal line contact which is a contact shape formed through linear contact, or other shapes which use asymmetric contact may be applicable to reduce a contact area. These contact shapes can produce the same effect as shown in FIG. 12. FIG. 19 shows an embodiment wherein a contact portion of the supporting column portion 36 with the heat-conducting member 22 is formed to be a projecting portion for point contact. FIG. 19(a) is a detailed, magnified view of the peripheral structure 37 of the heat transfer amount measuring unit and a cross-section along line B-C of FIG. 19(b). FIG. 19(b) shows a state viewed from point A of FIG. 19(a). FIG. 20 shows an embodiment wherein a contact portion of the supporting column portion 36 with the heat-conducting member 22 is formed to be a projecting portion for line contact in a longitudinal direction of the heat-conducting member. FIG. 20(a) is a detailed, magnified view of the peripheral structure 37 of the heat transfer amount measuring unit and a cross-section along line B–C of FIG. 20(b). FIG. 20(b) shows a state viewed from point A of FIG. 20(a). FIG. 21 shows an embodiment wherein a contact portion of the supporting column portion 36 with the heat-conducting member 22 is formed to be a projecting portion for point contact and the projecting portion is fixed at an adhesion site 45 of the heat-conducting member 22 with an adhesive agent. FIG. 21(a) is a detailed, magnified view of the peripheral configuration 37 of the heat transfer amount measuring unit and a cross-section along line B–C of FIG. 21(b). FIG. 21(b) shows a state viewed from point A of FIG. 21(a). FIG. 22 shows an embodiment wherein a contact portion of the supporting column portion 36 with the heat-conducting member 22 is formed to project from the supporting column portion 36 and to have a connection portion 46, and a holding portion 47 is formed to cover a circumferential surface of the heat-conducting member and to support it. FIG. 22(a) is a detailed, magnified view of the peripheral structure 37 of the heat transfer amount measuring unit and a cross-section along line B–C of FIG. 22(b). FIG. 22(b) shows a state viewed from point A of FIG. 22(a). In each case of FIGS. 19, 20, and 21, the contact portion of the supporting column portion 36 with the heat-conducting member 22, namely the end portion, is formed to have a smaller diameter at a position adjacent to the heat-conducting member than the diameters of the other portions of the supporting column portion 36, or at least the maximum diameter thereof. In the case of FIG. 22, the connection and holding portions are formed of a material having a lower heat conductivity than the supporting column portion.

Figure 13:
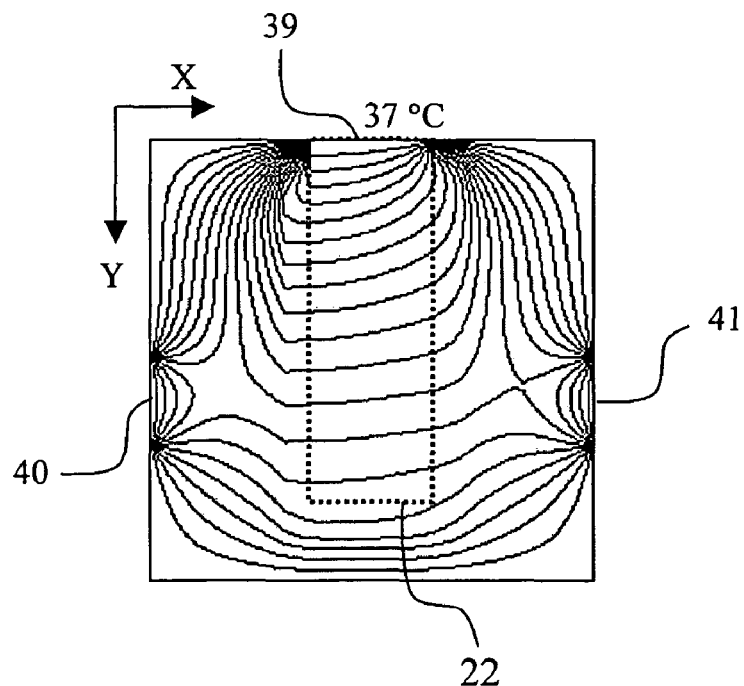
FIG. 13 shows a view for describing effects of one embodiment of the present invention.
Figure 14:
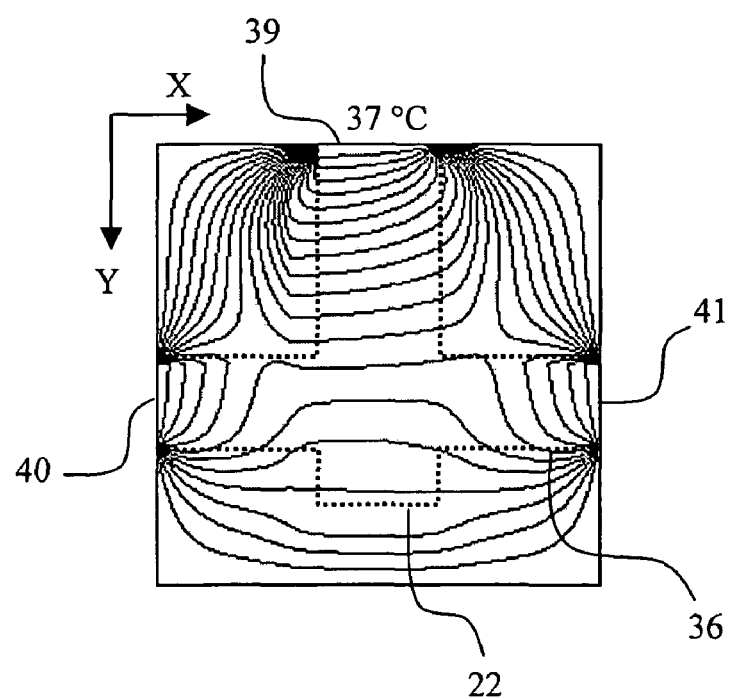
FIG. 14 shows a view for describing effects of one embodiment of the present invention.

The insulation effect when the insulation structure is employed will be described by referring to FIGS. 13 to 17. Herein, while a finger as heat source is in contact with the heat transfer amount measuring unit as shown above, the temperature distributions of the heat-conducting member 22 or supporting column portion 36 constituting the heat transfer amount measuring unit that are created are measured with a temperature measurement means such as a thermograph. FIGS. 13, 14, and 16 show the results of temperature distribution measurement with an isotherm, while the position of the heat-conducting member 22 or the supporting column portion 36 is indicated by a dotted line. The finger as heat source is in contact with a position represented as a reference numeral 39. Further, in FIGS. 15 and 17, left vertical axes indicate measured temperatures and right vertical axes indicate temperature difference. Furthermore, in each figure, an axis to be used for reading plots thereof is indicated by an arrow.

FIG. 13 shows a temperature distribution within the heat-conducting member 22 and of the surrounding space thereof when the heat-conducting member is present in the air, not in contact with any substance, and located at a substantial distance from the supporting column portion 36, while the heat-conducting member 22 is indicated by the dotted line. Heat-source-like points 40 and 41 at right and left sides are placed corresponding to the position of the supporting column portion 36, and the figure shows that the supporting column portion has a higher temperature than the surrounding air (ambience). Heat is conducted from a finger contact point at the upper part of the heat-conducting member 22, namely the contact point of the heat source to the inside of the heat-conducting member 22, and the temperature is almost equidistantly distributed. It is found that the heat flows evenly through the inside of the heat-conducting member 22 without the loss of the heat flux from the finger as heat source by avoiding contact with the supporting column member.

In contrast, FIG. 14 shows a temperature distribution within the heat-conducting member 22 and of the supporting column portion 36, and the surrounding space of the heat-conducting member 22, without the application of the present invention, while the heat-conducting member 22 and the contact portion of the supporting column portion 36 with the heat-conducting member are indicated by dotted lines. It is found that the intervals of the isotherm are quite different between the upper and lower connection portions between the heat-conducting member 22 and the supporting column portion 36. This indicates that the heat flux derived from the finger as heat source is varied. In other words, it indicates that the heat flux supplied from the heat source is affected at the supporting column portion 36 in contact therewith and that the heat flows towards the supporting column portion.

Figure 15:
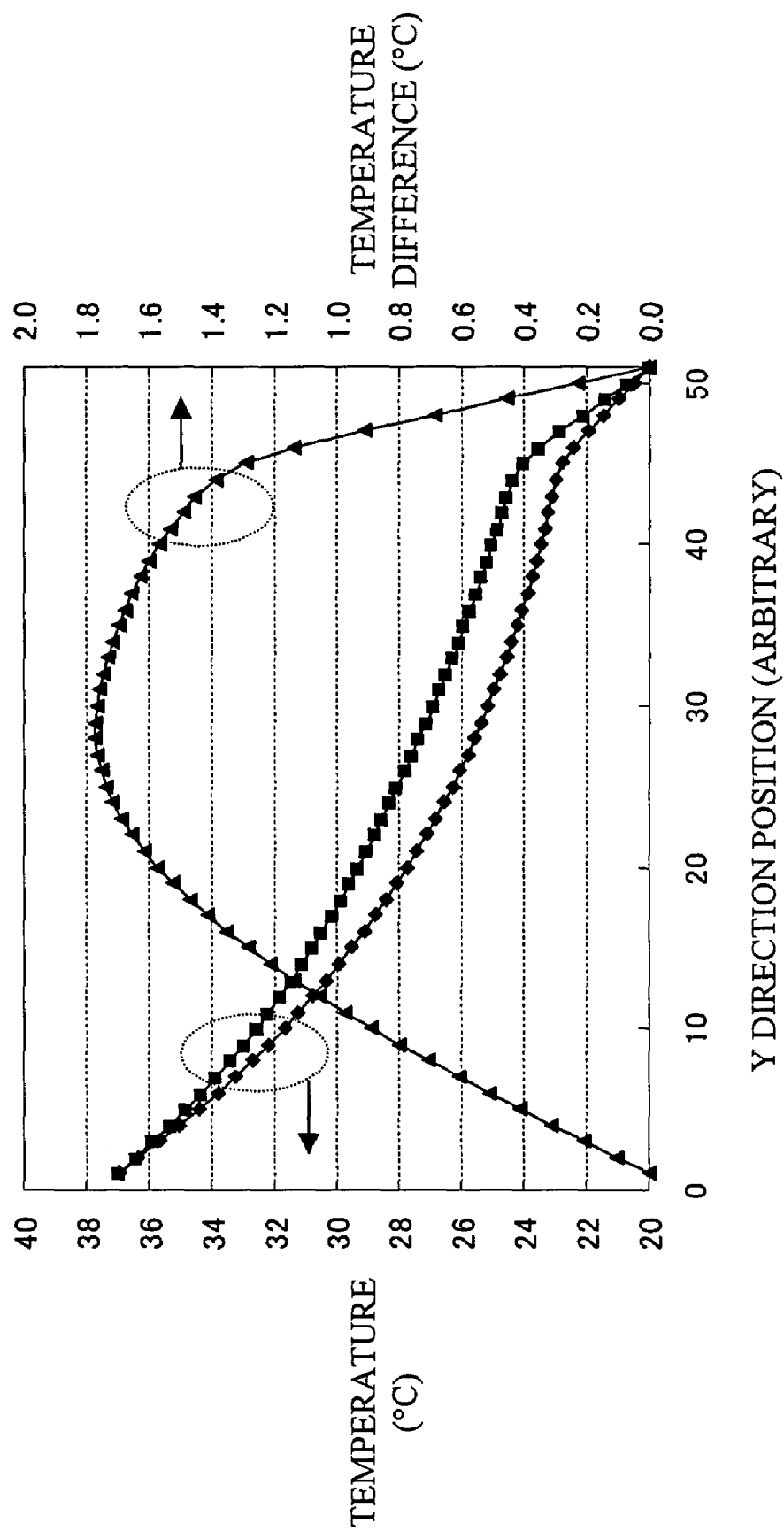
FIG. 15 shows a view for describing effects of one embodiment of the present invention.
Figure 16:
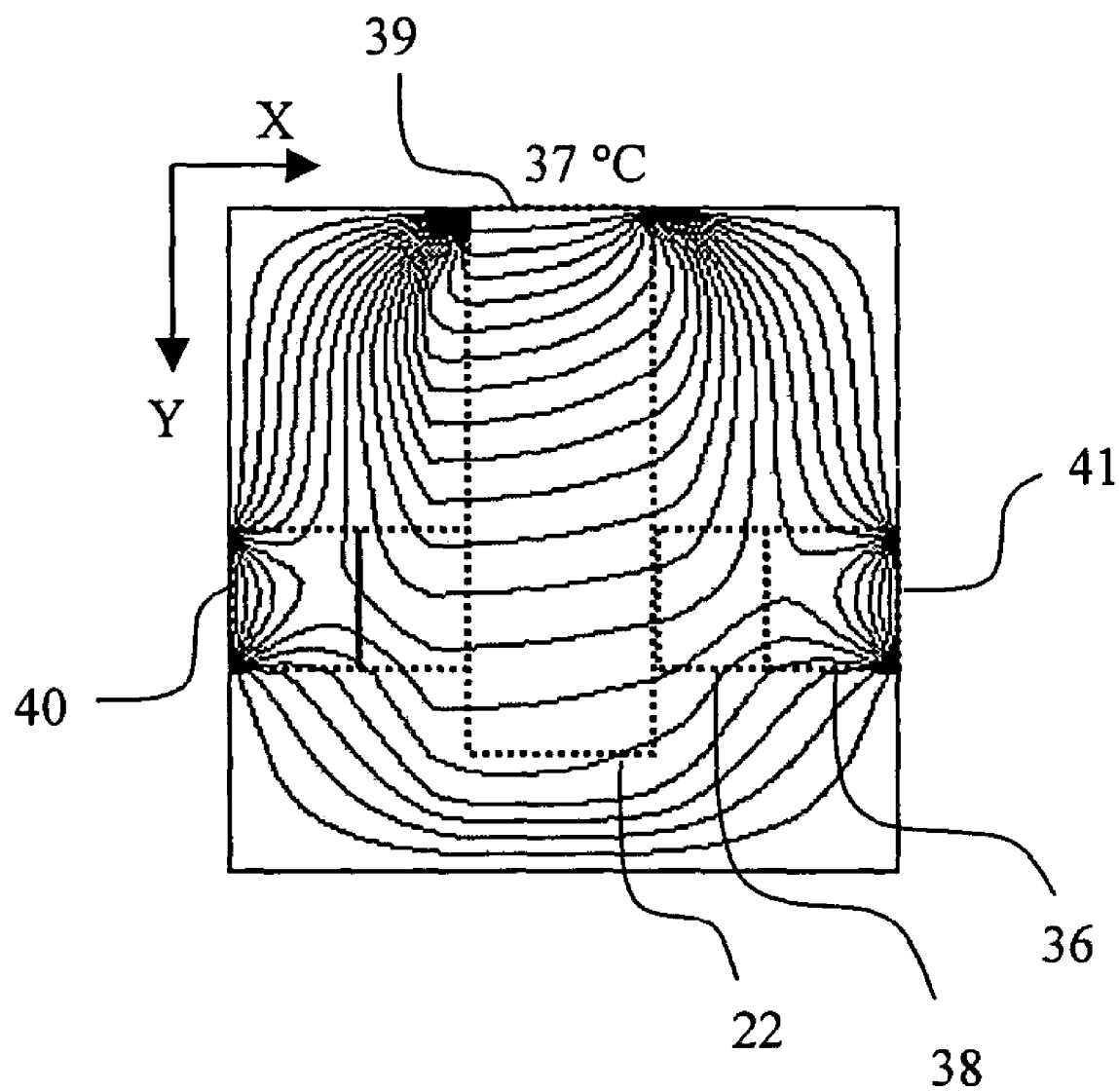
FIG. 16 shows a view for describing effects of one embodiment of the present invention.

FIG. 15 shows a comparison between the temperature distributions in the Y axis direction from the center of the heat-conducting member 22 in the X axis direction in the state of FIG. 13 and the state wherein the heat-conducting member 22 comes into contact with the supporting column portion 36 without the application of the present invention as described in FIG. 14. The temperatures measured in the state of FIG. 13 and the state of FIG. 14 and the measured temperature difference between their individual states are indicated by square plots, rhombic plots, and triangular plots, respectively. As shown in the figure, temperature measurement errors of up to 1.8° C. are found in the case of the state of FIG. 14 with respect to the state of FIG. 13.

Figure 17:
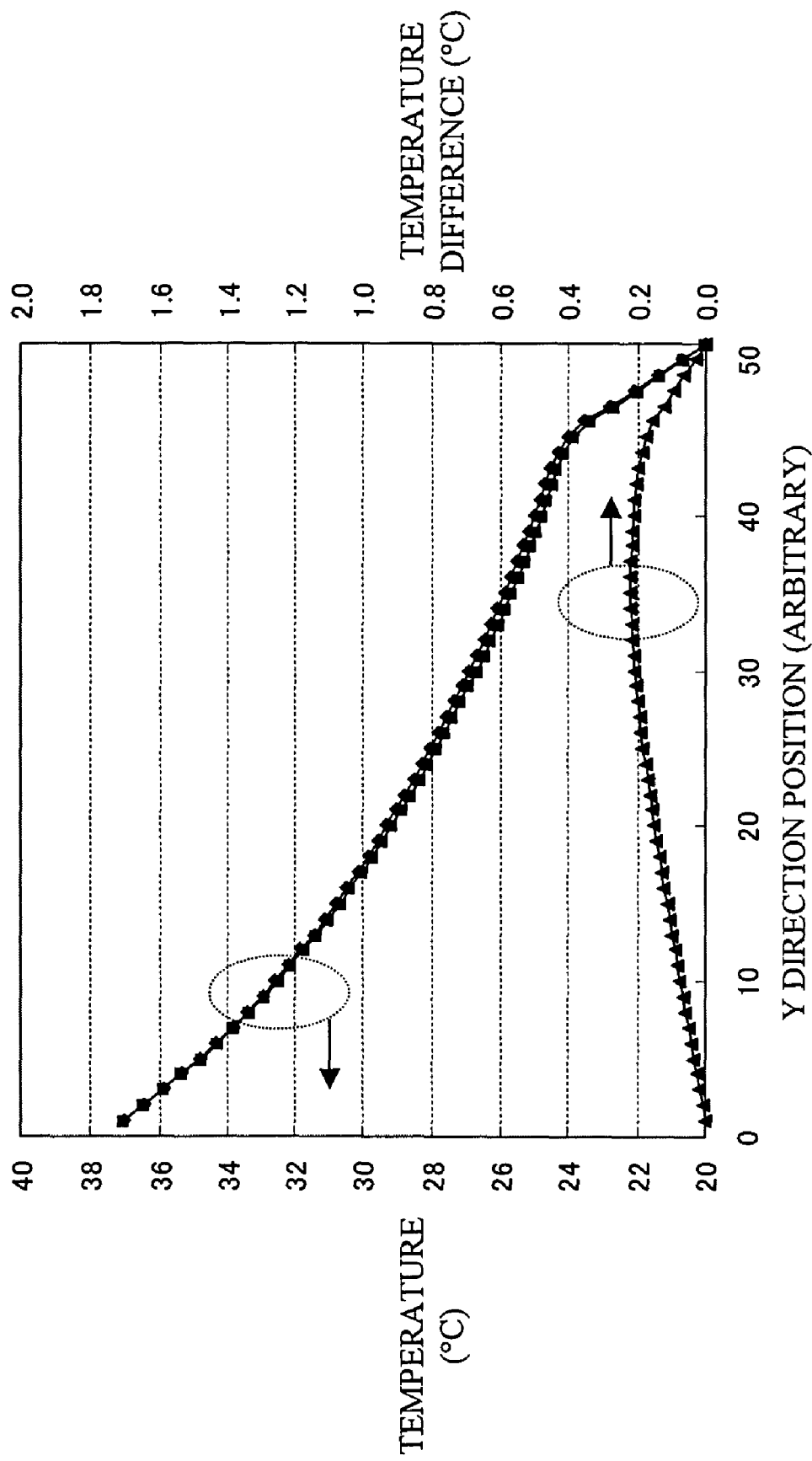
FIG. 17 shows a view for describing effects of one embodiment of the present invention.

FIG. 16 shows a temperature distribution of the inside of the heat-conducting member 22 and the supporting column portion 36 and the surrounding space of the heat-conducting member 22 when an insulator 38 is provided between the heat-conducting member 22 and the supporting column portion 36, where the heat-conducting member 22, the supporting column portion 36, and the insulator 38 are indicated by dotted lines. Further, FIG. 17 shows the comparison between the temperature distributions in the Y axis direction from the center of the heat-conducting member 22 in the X axis direction in the state of FIG. 13 and the state of FIG. 16. The temperatures measured in the state of FIG. 13, the state of FIG. 16, and the measured temperature difference between individual states of them are indicated by square plots, rhombic plots, and triangular plots, respectively.

It is found according to FIG. 16 that the temperature is equidistantly distributed inside the heat-conducting member 22 without the loss of the heat flux. In addition, according to the FIG. 17, when the temperature distribution of the state of FIG. 13 is compared with that of the FIG. 16, the temperature measurement differences therebetween are reduced to 0.2° C. at maximum in comparison with 1.8° C. in the case of FIG. 14 without the use of the insulator. According to these results, it can be confirmed that the heat flows almost evenly within the heat-conducting member 22 without the loss of the heat flux from the finger as heat source. It can also be confirmed that the occurrence of temperature measurement errors caused by the flow of the heat derived from the finger towards the supporting column portion is avoided by using insulators to avoid direct contact between the supporting column member and the heat-conducting member.

An infrared lens 25 is disposed inside the apparatus at such a position that the measured object (ball of the finger) placed on the finger rest 15 can be seen through the lens.

Below the infrared lens 25 is disposed a pyroelectric detector 27 via an infrared radiation-transmitting window 26. Another thermistor 28 is disposed near the pyroelectric detector 27.

Figure 7C:
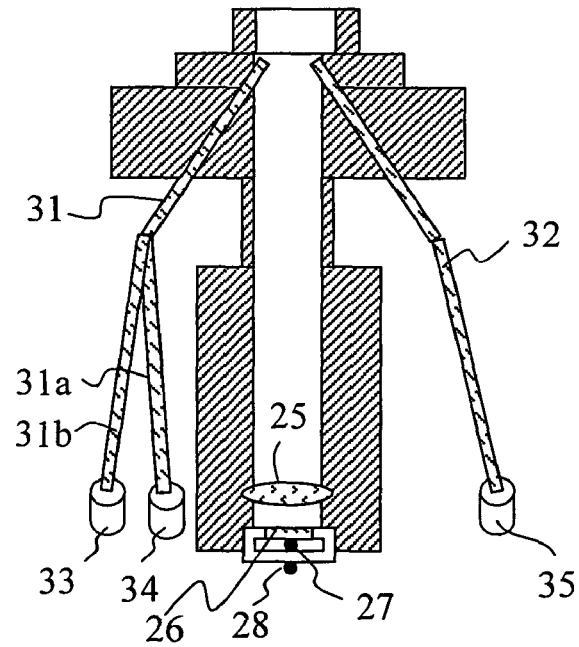

Thus, the temperature sensor portion of the measuring unit has four temperature sensors, and they measure four kinds of temperatures as follows:

(1) Temperature on the finger surface (thermistor 23): $T_1$
(2) Temperature of the heat-conducting member (thermistor 24): $T_2$
(3) Temperature of radiation from the finger (pyroelectric detector 27): $T_3$
Room temperature (thermistor 28): $T_4$ The optical sensor unit 18 measures the hemoglobin concentration and the hemoglobin oxygen saturation necessary for the determination of the oxygen supply volume. In order to measure the hemoglobin concentration and the hemoglobin oxygen saturation, absorption must be measured at at least two wavelengths. FIG. 7(c) shows a configuration for carrying out the two-wavelength measurement using two light sources 33 and 34 and one detector 35.

The optical sensor unit 18 includes the ends of two optical fibers 31 and 32. The optical fiber 31 is for optical irradiation, and the optical fiber 32 is for receiving light. As shown in FIG. 7(c), the optical fiber 31 connects to branch fibers 31a and 31b that are provided with light-emitting diodes 33 and 34 at the respective ends thereof. The other end of the light-receiving optical fiber 32 is provided with a photodiode 35. The light-emitting diode 33 emits light with a wavelength of 810 nm, while the light-emitting diode 34 emits light with a wavelength of 950 nm. The wavelength 810 nm is the equal absorption wavelength at which the molar absorbance coefficient of the oxy-hemoglobin is equal to that of the deoxy-hemoglobin. The wavelength 950 nm is the wavelength at which the difference between the molar absorbance coefficient of the oxy-hemoglobin and that of the deoxy-hemoglobin is large.

The two light-emitting diodes 33 and 34 emit light in a time-sharing manner such that the finger of the subject is irradiated with the light emitted by the light-emitting diodes 33 and 34 via the irradiating optical fiber 31. The light shone on the finger is reflected by the skin, enters the light-receiving optical fiber 32, and is eventually detected by the photodiode 35. Part of the light reflected by the skin of the finger penetrates the skin and enters into the tissues and is then absorbed by the hemoglobin in the blood flowing in the capillary blood vessels. The measurement data provided by the photodiode 35 has reflectance R, and the absorbance can be approximately calculated by log(1/R). The finger is thus irradiated with light with the wavelengths of 810 nm and 950 nm, and R is measured for each and also log(1/R) is calculated for each. Thus, absorption $A_1$ and $A_2$ for wavelengths 810 nm and 950 nm, respectively, are measured.

When the deoxy-hemoglobin concentration is [Hb] and the oxy-hemoglobin concentration is [HbO$_2$], absorption $A_1$ and $A_2$ are expressed by the following equations:

$$A_1 = a \times ([Hb] \times A_{Hb}(810\,\text{nm}) + [HbO_2] \times A_{HbO_2}(810\,\text{nm}))$$

$$= a \times ([Hb] + [HbO_2]) \times A_{HbO_2}(810\,\text{nm})$$

$$A_2 = a \times ([Hb] \times A_{Hb}(950\,\text{nm}) + [HbO_2] \times A_{HbO_2}(950\,\text{nm}))$$

$$= a \times ([Hb] + [HbO_2]) \times \left(\left(1 - \frac{[HbO_2]}{[Hb]+[HbO_2]}\right) \times A_{Hb}(950\,\text{nm}) + \right.$$

-continued
$$\left. \frac{[HbO_2]}{[Hb]+[HbO_2]} \times A_{HbO_2}(950\,\text{nm})\right)$$

$A_{Hb}(810\,\text{nm})$ and $A_{Hb}(950\,\text{nm})$, and $A_{HbO_2}(810\,\text{nm})$ and $A_{HbO_2}(950\,\text{nm})$ are the molar absorbance coefficients of the deoxy-hemoglobin and the oxy-hemoglobin, respectively, and are known at the respective wavelengths. The term a is a proportionality coefficient. The hemoglobin concentration [Hb]+[HbO$_2$], and the hemoglobin oxygen saturation [HbO$_2$]/([Hb]+[HbO$_2$]) can be determined from the above equations as follows:

$$[Hb] + [HbO_2] = \frac{A_1}{a \times A_{HbO_2}(810\,\text{nm})}$$

$$\frac{[HbO_2]}{[Hb]+[HbO_2]} = \frac{A_2 \times A_{HbO_2}(810\,\text{nm}) - A_1 \times A_{Hb}(950\,\text{nm})}{A_1 \times (A_{HbO_2}(950\,\text{nm}) - A_{Hb}(950\,\text{nm}))}$$

In the present example, the hemoglobin concentration and the hemoglobin oxygen saturation are measured by measuring absorbance at two wavelengths. Preferably, however, absorbance may be measured at more than two wavelengths so that the influence of interfering components can be reduced and measurement accuracy can be improved.

Specific examples of major interfering components include melanin pigment to determine skin color, bilirubin as a causative substance of jaundice symptom, and blood turbidity as a cause of hyperlipidemia. As one example, it is possible to reduce the influence of the interfering components and enhance the measurement accuracy by adding lights with wavelengths of 535 nm, 470 nm, and 660 nm, each of which may be used for observing large molar absorbance coefficients of melanin pigment, bilirubin, and blood turbidity, respectively. It should be noted that the wavelength values described in this specification, including the wavelengths of 810 nm and 950 nm described above for use with respect to the oxy-hemoglobin and deoxy-hemoglobin, are the values most suitable to obtain individual absorbances of interest, such as to obtain absorbance at a wavelength where molar absorbance coefficients are equal, or to obtain peaks of absorbances. Therefore, wavelengths of roughly those described in the present specification, that is wavelengths of about 20 nm above or below the described wavelengths, can be used similarly for measurement.

Figure 8:
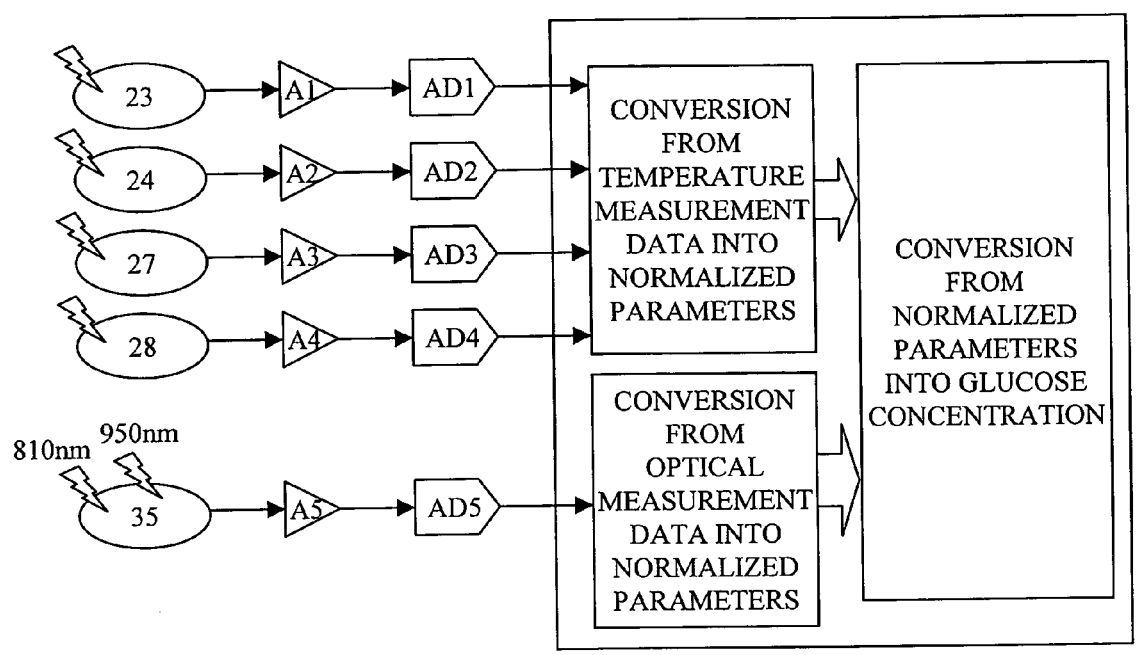
FIG. 8 shows a conceptual chart illustrating the flow of data processing in the apparatus.

FIG. 8 shows the concept of how data is processed in the apparatus. The apparatus according to the present example is equipped with five sensors, namely thermistor 23, thermistor 24, pyroelectric detector 27, thermistor 28, and photodiode 35. The photodiode 35 measures absorption at wavelengths 810 nm and 950 nm. Thus, the apparatus is supplied with six kinds of measurement values.

The five kinds of analog signals are supplied via individual amplifiers $A_1$ to $A_5$ to analog/digital converters $AD_1$ to $AD_5$, where they are converted into digital signals. Based on the digitally converted values, parameters $x_i$ (i=1, 2, 3, 4, 5) are calculated. The following are specific descriptions of $x_i$ (where $a_1$ to $a_5$ are proportionality coefficients):

Parameter proportional to heat radiation $$X_1 = a_1 \times (T_3)^4$$

Parameter proportional to heat convection $$x_2 = a_2 \times (T_4 - T_3)$$

Parameter proportional to hemoglobin concentration $$x_3 = a_3 \times \left(\frac{A_1}{a \times A_{HbO_2}(810 \text{ nm})}\right)$$

Parameter proportional to hemoglobin saturation $$x_4 = a_4 \times \left(\frac{A_2 \times A_{HbO_2}(810 \text{ nm}) - A_1 \times A_{Hb}(950 \text{ nm}))}{A_1 \times (A_{HbO_2}(950 \text{ nm}) - A_{Hb}(950 \text{ nm}))}\right)$$

Parameter proportional to blood flow volume $$x_5 = a_5 \times \left(\frac{1}{t_{CONT} \times (S_1 - S_2)}\right)$$

In terms of $S_1$ and $S_2$ used in the calculation of the parameter $x_5$ proportional to blood flow volume, it has been confirmed that the application of the above insulation structure or structure for the reduction of the heat conductivity can reduce measurement errors from conventionally about 10% to about 0.1% with respect to the measured value in the state of FIG. 13 wherein the heat-conducting member is not in contact with the supporting column portion. Although the values of $S_1$ and $S_2$ are determined by measured temperature and measured time, the absolute value of the measured temperature is changed by applying the insulation structure or the structure for the reduction of the heat conductivity between the heat-conducting member and the supporting column portion. As described above, there is a measured value difference of nearly 2° C. between cases with and without the application of the above structures. Further, the temperature difference is caused by the loss of a part of the heat that should be normally measured due to an absence of the application of the above structures. Therefore, this should be regarded as a temperature measurement error.

For example, when the temperature $T_1$ used in the determination of $S_1$ is 37° C. and the temperature $T_2$ used in the determination of $S_2$ is measured at 24° C. with the application of the above configurations, the temperature $T_2$ without the application of the above structures may be measured at about 22° C.

When the measured times (contact time with the heat source) are equal, the values $S_1$ and $S_2$ are substantially proportional to the measured temperature although they are obtained by integration with respect to the time. These values are substituted into the parameter $x_5$ proportional to the blood flow volume and the proportionality coefficient $a_5$ is kept constant. Then, the above case is taken as an example wherein when $T_1$ is 37° C., $T_2$ with the application of the insulation structure or the structure for the reduction of the heat conductivity is 24° C. and $T_2$ without the application the structure is 22° C. In the example, $x_5$ is calculated and compared as below. Here, values $S_1$ and $S_2$ are products of individual measured temperatures and measured times ($t_{count}$) for simplicity.

$$S_1 = T_1 \times t_{count}$$

$$S_2 = T_2 \times t_{count}$$

$$X_5 = a_5/(t_{count} \times (S_1 - S_2)) \text{ (definition of } X_5\text{)}$$

[when the insulation structure or the structure for the reduction of the heat conductivity is applied, $X_5$ is expressed as $X_5 \text{ }_{applied}$]

$$X_{5 \text{ }applied} = a_5/(t_{count} \times (37-24) \times t_{count})$$

[when the insulation structure or the structure for the reduction of the heat conductivity is not applied, $X_5$ is expressed as $X_{5 \text{ }not\text{-}applied}$]

$$X_{5 \text{ }not\text{-}applied}(\text{application}) = a^5/(t_{count} \times (37-22) \times t_{count})$$

[proportion between $X_5$ applied and $X_5 \text{ }_{not\text{-}applied}$]

$$X_{5applied} : X_{5not\text{-}applied} = 1/13 : 1/15 = 0.077 : 0.066 =: 1:0.85$$

The value $X_5$ (=$X_{5applied}$) with the application of the insulation structure or the structure for the reduction of the heat conductivity differs by 15% from $X_5$ (=$X_{5not\text{-}applied}$) without the application of the structures. This difference means that there is an improvement of accuracy. The measured temperature difference of 2° C. between cases with and without the application of the structures is regarded as a measurement error, because when the structure is applied, it is confirmed that the measurement conditions are desired on the basis of the review of the above temperature distribution.

Then, normalized parameters are calculated from mean values and standard deviations of $x_i$ obtained by actual data pertaining to large numbers of able-bodied people and diabetic patients. A normalized parameter $X_1$ (where i=1, 2, 3, 4, 5) is calculated from each parameter $x_i$ according to the following equation:

$$X_i = \frac{x_i - \bar{x}_i}{SD(x_i)}$$

where $x_i$: parameter $\bar{x}_i$: mean value of the parameter $SD(x_i)$: standard deviation of the parameter Using the above five normalized parameters, calculations are conducted for conversion into glucose concentration to be eventually displayed. A program necessary for the processing calculations is stored in a ROM in the microprocessor built inside the apparatus. The memory region required for the processing calculations is ensured in a RAM similarly built inside the apparatus. The results of calculation are displayed on the LCD display.

The ROM stores, as a constituent element of the program necessary for the processing calculations, a function for determining glucose concentration C in particular. The function is defined as follows. C is expressed by the below-indicated equation (1), where $a_i$ (i=0, 1, 2, 3, 4, 5) is determined from a plurality of pieces of measurement data in advance according to the following procedure:

(1) A multiple regression equation is created that indicates the relationship between the normalized parameter and the glucose concentration C.

(2) A normalized equation (simultaneous equation) relating to the normalized parameter is obtained from an equation obtained by the least-squares method.

(3) Values of coefficient $a_i$ (i=0, 1, 2, 3, 4, 5) are determined from the normalized equation and then substituted into the multiple regression equation.

Initially, the regression equation (1) indicating the relationship between the glucose concentration C and the normalized parameters $X_1$, $X_2$, $X_3$, $X_4$, and $X_5$ is formulated.

$$C = f(X_1, X_2, X_3, X_4, X_5) \qquad (1)$$
$$= a_0 + a_1 X_1 + a_2 X_2 + a_3 X_3 + a_4 X_4 + a_5 X_5$$

Then, the least-squares method is employed to obtain a multiple regression equation that would minimize the error with respect to a measured value Ci of glucose concentration according to an enzyme electrode method. When the sum of squares of the residual is D, D is expressed by the following equation (2):

$$D = \sum_{i=1}^{n} d_i^2 \qquad (2)$$
$$= \sum_{i=1}^{n} (C_i - f(X_{i1}, X_{i2}, X_{i3}, X_{i4}, X_{i5}))^2$$
$$= \sum_{i=1}^{n} \{C_i - (a_0 + a_1 X_{i1} + a_2 X_{i2} + a_3 X_{i3} + a_4 X_{i4} + a_5 X_{i5})\}^2$$

Because the sum of squares of the residual D becomes minimum when partial differentiation of equation (2) with respect to $a_0$, $a_2$, . . . , $a_5$ gives zero. Thus, we have the following equations:

(3)

$$\frac{\partial D}{\partial a_0} = -2 \sum_{i=1}^{n} \{C_i - (a_0 + a_1 X_{i1} + a_2 X_{i2} + a_3 X_{i3} + a_4 X_{i4} + a_5 X_{i5})\} = 0$$

$$\frac{\partial D}{\partial a_1} = -2 \sum_{i=1}^{n} X_{i1}\{C_i - (a_0 + a_1 X_{i1} + a_2 X_{i2} + a_3 X_{i3} + a_4 X_{i4} + a_5 X_{i5})\} = 0$$

$$\frac{\partial D}{\partial a_2} = -2 \sum_{i=1}^{n} X_{i2}\{C_i - (a_0 + a_1 X_{i1} + a_2 X_{i2} + a_3 X_{i3} + a_4 X_{i4} + a_5 X_{i5})\} = 0$$

$$\frac{\partial D}{\partial a_3} = -2 \sum_{i=1}^{n} X_{i3}\{C_i - (a_0 + a_1 X_{i1} + a_2 X_{i2} + a_3 X_{i3} + a_4 X_{i4} + a_5 X_{i5})\} = 0$$

$$\frac{\partial D}{\partial a_4} = -2 \sum_{i=1}^{n} X_{i4}\{C_i - (a_0 + a_1 X_{i1} + a_2 X_{i2} + a_3 X_{i3} + a_4 X_{i4} + a_5 X_{i5})\} = 0$$

$$\frac{\partial D}{\partial a_5} = -2 \sum_{i=1}^{n} X_{i5}\{C_i - (a_0 + a_1 X_{i1} + a_2 X_{i2} + a_3 X_{i3} + a_4 X_{i4} + a_5 X_{i5})\} = 0$$

When the mean values of C and $X_1$ to $X_5$ are $C_{mean}$ and $X_{1mean}$ to $X_{5mean}$, respectively, since $X_{imean}=0$ (i=1 to 5), equation (4) can be obtained from equation (1) thus:

$$a_0 = C_{mean} - a_1 X_{1mean} - a_2 X_{2mean} - a_3 X_{3mean} - a_4 X_{4mean} - a_5 X_{5mean} \qquad (4)$$

$$= C_{mean}$$

The variation and covariation between the normalized parameters are expressed by equation (5). Covariation between the normalized parameter $X_i$ (i=1 to 5) and C is expressed by equation (6).

$$S_{ij} = \sum_{k=1}^{n} (X_{ki} - X_{imean})(X_{kj} - X_{jmean}) = \sum_{k=1}^{n} X_{ki} X_{kj} \quad (i, j = 1, 2, \ldots 5) \qquad (5)$$

$$S_{iC} = \qquad (6)$$
$$\sum_{k=1}^{n} (X_{ki} - X_{imean})(C_k - C_{mean}) = \sum_{k=1}^{n} X_{ki}(C_k - C_{mean}) \quad (i = 1, 2, \ldots 5)$$

Substituting equations (4), (5), and (6) into equation (3) and rearranging yields simultaneous equation (normalized equation) (7). Solving equation (7) yields $a_1$ to $a_5$.

$$a_1 S_{11} + a_2 S_{12} + a_3 S_{13} + a_4 S_{14} + a_5 S_{15} = S_{1C}$$

$$a_1 S_{12} + a_2 S_{22} + a_3 S_{23} + a_4 S_{24} + a_5 S_{25} = S_{2C}$$

$$a_1 S_{31} + a_2 S_{32} + a_3 S_{33} + a_4 S_{34} + a_5 S_{35} = S_{3C}$$

$$a_1 S_{41} + a_2 S_{42} + a_3 S_{43} + a_4 S_{44} + a_5 S_{45} = S_{4C}$$

$$a_1 S_{51} + a_2 S_{52} + a_3 S_{53} + a_4 S_{54} + a_5 S_{55} = S_{5C} \qquad (7)$$

Constant term $a_0$ is obtained by means of equation (4). The thus obtained $a_i$ (i=0, 1, 2, 3, 4, 5) is stored in ROM at the time of manufacture of the apparatus. In actual measurement using the apparatus, the normalized parameters $X_1$ to $X_5$ obtained from the measured values are substituted into regression equation (1) to calculate the glucose concentration C.

Hereafter, an example of the process of calculating the glucose concentration will be described. First, the coefficients in equation (1) are determined in advance based on large data obtained from able-bodied persons and diabetic patients, using the apparatus without the application of the above insulation structure or the structure for the reduction of the heat conductivity. The ROM in the microprocessor stores the following formula for the calculation of glucose concentration:

$$C = 99.4 + 18.3 \times X_1 - 20.2 \times X_2 - 23.7 \times X_3 - 22.0 \times X_4 - 25.9 \times X_5$$

$X_1$ to $X_5$ are the results of normalization of parameters $x_1$ to $x_5$. Assuming the distribution of the parameters is normal, 95% of the normalized parameter takes on values between $-2$ to $+2$. In the case of an able-bodied person, substituting exemplary measurement values in the above equation such that normalized parameters $X_1=-0.06$, $X_2=+0.04$, $X_3=+0.05$, $X_4=-0.12$, and $X_5=+0.10$ yields $C=96.4$ mg/dl. In the case of a diabetic patient, substituting exemplary measurement values in the equation such that normalized parameters $X_1=+1.15$, $X_2=-1.02$, $X_3=-0.83$, $X_4=-0.91$, and $X_5=-1.24$ yields $C=212.8$ mg/dl. Meanwhile, when the apparatus employing the above insulation structure or the heat conductivity reduction structure is used, the normalized parameter $X_5$ is changed as the measurement error for the parameter $x_5$ is reduced by about 15% as described above. The change of the normalized parameter changes the coefficient for parameter $X_5$ of the regression equation indicating the relationship between the glucose concentration C and the normalized parameters. Therefore, the coefficient for the parameter $X_5$ is changed from 25.9 to 29.8 as follows. The ROM in the microprocessor stores the following formula for the calculation of glucose concentration.

$$C=99.4+18.3 \times X_1 - 20.2 \times X_2 - 23.7 \times X_3 - 22.0 \times X_4 - 29.8 \times X_5$$

In the case of an able-bodied person, substituting exemplary measurement values in the above equation such that normalized parameters $X_1=-0.06$, $X_2=+0.04$, $X_3=+0.05$, $X_4=-0.12$, and $X_5=+0.10$ yields $C=95.9$ mg/dl. In the case of a diabetic patient, substituting exemplary measurement values in the equation such that normalized parameters $X_1=+1.15$, $X_2=-1.02$, $X_3=-0.83$, $X_4=-0.91$, and $X_5=-1.24$ mg/dl.

Figure 9:
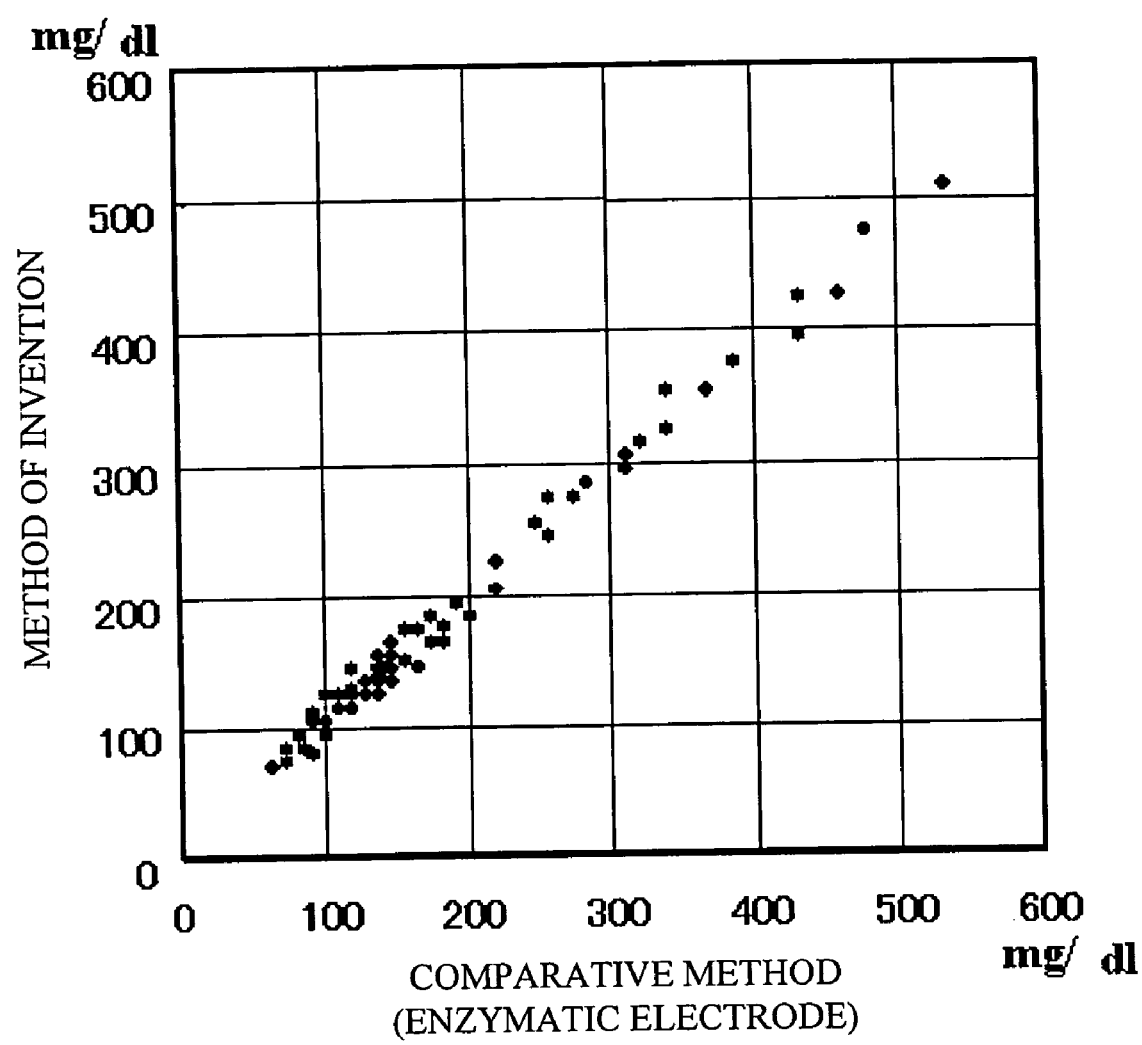
FIG. 9 shows the plots of the glucose concentration values calculated according to the present invention and the glucose concentration values measured by the enzymatic electrode method.

The measurement by the enzymatic electrode method was conducted at the same time that the above examples were conducted. In the enzymatic electrode method, a blood sample was reacted with a reagent and the amount of resultant electrons was measured to determine glucose concentration. The glucose concentration for an able-bodied person was 89 mg/dl according to the enzymatic electrode method. As described above, the glucose concentration measured at the same time as the above examples by the apparatus without the application of the insulation structure or the heat conductivity reduction structure was $C=96.4$ mg/dl, whereas the glucose concentration measured by the apparatus with the application of the above configuration was $C=95.9$ mg/dl. It is therefore confirmed that the apparatus with the application of the configuration could provide a value closer to the value measured by blood sampling and highly accurate measurement. Further, the glucose concentration for the diabetic patient was measured according to the enzymatic electrode method in the same manner at the same time as the above example, and was found to be 238 mg/dl. As described above, the glucose concentration measured by the apparatus without the application of the insulation structure or the heat conductivity reduction structure was $C=212.8$ mg/dl, though the glucose concentration measured by the apparatus with the application of the above structure was $C=217.7$ mg/dl. It is therefore confirmed that when the apparatus with the application of the structure is used for the diabetic patient, it could provide a value closer to the value measured by blood sampling and highly accurate measurement in the same manner as in the case of the able-bodied person. The results thus indicated that the method according to the invention could provide highly accurate measurement of glucose concentration. FIG. 9 shows the plot of glucose concentration for a plurality of patients. The calculated values of glucose concentration according to the invention are shown on the vertical axis, and the measured values of glucose concentration according to the enzymatic electrode method are shown on the horizontal axis. It will be seen that a good correlation can be obtained by measuring the oxygen supply volume and the blood flow volume according to the method of the invention (correlation coefficient=0.9524).

Thus, the invention can provide a highly accurate non-invasive blood sugar level measuring apparatus and method.

What is claimed is:

1. A blood sugar level measuring apparatus comprising:
   a heat amount measuring unit for measuring a plurality of temperatures derived from the body surface in order to obtain information used for calculating the amount of convective heat transfer and the amount of radiation heat transfer concerning the dissipation of heat from the body surface;
   an oxygen volume measuring unit for obtaining information concerning the volume of blood oxygen;
   a storage unit for storing the relationships between the individual parameters corresponding to the multiple temperatures and blood oxygen volume and blood sugar levels;
   a computing unit for converting the measurement values provided by the heat amount measuring unit and the oxygen volume measuring unit into parameters, and computing a blood sugar level by applying the parameters to the relationships stored in the storage unit; and
   a display unit for displaying the blood sugar level computed by the computing unit,
   wherein the oxygen volume measuring unit comprises a blood flow volume measuring unit for obtaining information concerning the volume of blood flow and a heat transfer prevention means for preventing heat transfer to the blood flow volume measuring unit from the vicinity thereof, wherein the blood flow volume measuring unit comprises:
   a body-surface contact unit;
   an adjacent temperature detector disposed adjacent the body-surface contact unit;
   an indirect temperature detector for detecting the temperature at a position distanced away from the body-surface contact unit; and
   a heat-conducting member connecting the body-surface contact unit and the indirect temperature detector, wherein
   the heat transfer prevention means prevents heat transfer to the heat-conducting member.

2. The blood sugar level measuring apparatus according to claim 1, further comprising at least one supporting column member for installing the blood flow volume measuring unit,
   wherein the heat transfer prevention means is a heat insulator disposed between the heat-conducting member and the supporting column member and the heat insulator has a smaller heat conductivity than the supporting column member.

3. The blood sugar level measuring apparatus according to claim 2, wherein the heat insulator is formed of a material having the properties of any of a fiber material, a foaming material, or a micro dust layer material.

4. The blood sugar level measuring apparatus according to claim 2, wherein the heat insulator has a heat conductivity of 0.0005 W/mK to 0.02 W/mK.

5. The blood sugar level measuring apparatus according to claim 1, further comprising at least one supporting column member for installing the blood flow volume measuring unit, wherein the heat transfer prevention means is an end part of the supporting column member which is adjacent to the heat-conducting member and has a smaller diameter at a position adjacent to the heat-conducting member than the maximum diameter of the supporting column member.

6. The blood sugar level measuring apparatus according to claim 5, wherein the end part has point contact with the heat-conducting member.

7. The blood sugar level measuring apparatus according to claim 5, wherein the end part has linear contact with the heat-conducting member.

8. The blood sugar level measuring apparatus according to claim 1, further comprising at least one supporting column member for installing the blood flow volume measuring unit, wherein
the heat transfer prevention means comprises a connecting part projecting from the supporting column member and a holding part which is connected to the connecting part and holds the heat-conducting member.

9. The blood sugar level measuring apparatus according to claim 1, wherein the oxygen volume measuring unit further comprises an optical measuring unit for obtaining blood hemoglobin concentration and hemoglobin oxygen saturation.

10. The blood sugar level measuring apparatus according to claim 9, wherein the optical measuring unit comprises:
a light source for generating light of at least two different wavelengths;
an optical system for irradiating the body surface with light emitted by the light source; and
a photodetector for detecting the light with which the body surface has been irradiated.

11. The blood sugar level measuring apparatus according to claim 1, wherein the heat amount measuring unit comprises:
an ambient temperature detector for measuring the ambient temperature; and
a radiation temperature detector for measuring the radiation heat from the body surface.

12. A blood sugar level measuring apparatus comprising:
an ambient temperature measuring unit for measuring the ambient temperature;
a body-surface contact unit to be brought into contact with a body surface;
a radiation heat detector for measuring the radiation heat from the body surface;
a heat-conducting member disposed in contact with the body-surface contact unit;
a heat insulator disposed in contact with the heat-conducting member;
a contact part for covering an open end of the heat-conducting member in contact with the body-surface contact unit;
an adjacent temperature detector for detecting the temperature of the contact part;
an indirect temperature detector disposed adjacent the heat-conducting member and away from the body-surface contact unit for detecting the temperature at a position distanced away from the body-surface contact unit;
a light source for irradiating the body-surface contact unit with light of at least two different wavelengths;
a photodetector for detecting the light with which the body surface has been irradiated;
a converting unit for converting the outputs from the adjacent temperature detector, the indirect temperature detector, the ambient temperature measuring unit, the radiation heat detector, and the photodetector into individual parameters;
a storage unit for storing the relationships between the parameters and blood sugar levels;
a computing unit for computing a blood sugar level by applying the individual parameters to the relationships stored in the storage unit; and
a display unit for displaying the blood sugar level produced from the computing unit.

13. The blood sugar level measuring apparatus according to claim 12, further comprising at least one supporting column member for installing the heat-conducting member, wherein the heat insulator has a lower heat conductivity than the supporting column member.

14. The blood sugar level measuring apparatus according to claim 12, further comprising at least one supporting column member for installing the heat-conducting member, wherein the heat insulator is disposed between the heat-conducting member and the supporting column member.

15. A blood sugar level measuring apparatus comprising:
an ambient temperature measuring unit for measuring the ambient temperature;
a body-surface contact unit to be brought into contact with a body surface;
a radiation heat detector for measuring the radiation heat from the body surface;
a heat-conducting member disposed in contact with the body-surface contact unit;
a supporting column member which supports the heat-conducting member and has a smaller diameter at a site adjacent to the heat-conducting member than the maximum diameter of the supporting column member;
a contact part for covering an open end of the heat-conducting member in contact with the body-surface contact unit;
an adjacent temperature detector for detecting the temperature of the contact part;
an indirect temperature detector disposed adjacent the heat-conducting member and away from the body-surface contact unit for detecting the temperature at a position distanced away from the body-surface contact unit;
a light source for irradiating the body-surface contact unit with light of at least two different wavelengths;
a photodetector for detecting the light with which the body surface has been irradiated;
a converting unit for converting the outputs of the adjacent temperature detector, the indirect temperature detector, the ambient temperature measuring unit, the radiation heat detector, and the photodetector into individual parameters;
a storage unit for storing the relationships between the parameters and blood sugar levels;
a computing unit for computing a blood sugar level by applying the individual outputs to the relationships stored in the storage unit; and a display unit for displaying the blood sugar level produced from the computing unit.

16. The blood sugar level measuring apparatus according to claim 15, wherein the end part has a smaller diameter at a site adjacent to the heat-conducting member than the other parts of the supporting column member.

17. The blood sugar level measuring apparatus according to claim 15, wherein the end part is in contact with the heat-conducting member through linear contact.

18. The blood sugar level measuring apparatus according to claim 15, wherein the end part is in contact with the heat-conducting member through point contact.

* * * * *